US012770120B2

(12) United States Patent
Short

(10) Patent No.: US 12,770,120 B2
(45) Date of Patent: Oct. 20, 2026

(54) SYSTEMS AND METHODS FOR MULTI-LAYER ADAPTIVE PACKET ROUTING

(71) Applicant: William C. Short, Dallas, TX (US)

(72) Inventor: William C. Short, Dallas, TX (US)

(73) Assignee: Accresa Health LLC, Carrollton, TX (US)

( * ) Notice: Subject to any disclaimer, the term of this patent is extended or adjusted under 35 U.S.C. 154(b) by 449 days.

(21) Appl. No.: 17/468,351

(22) Filed: Sep. 7, 2021

(65) Prior Publication Data

US 2021/0406848 A1 Dec. 30, 2021

Related U.S. Application Data

(63) Continuation-in-part of application No. 16/449,111, filed on Jun. 21, 2019, now abandoned, which is a continuation of application No. 16/018,524, filed on Jun. 26, 2018, now abandoned.

(51) Int. Cl.

| | |
|---|---|
| ***G06Q 20/10*** | (2012.01) |
| ***G06Q 20/40*** | (2012.01) |
| ***G06Q 30/04*** | (2012.01) |
| ***G16H 10/60*** | (2018.01) |
| ***G16H 40/20*** | (2018.01) |
| ***H04L 45/28*** | (2022.01) |

(52) U.S. Cl.

CPC ......... *G06Q 20/102* (2013.01); *G06Q 20/105* (2013.01); *G06Q 20/40* (2013.01); *H04L 45/28* (2013.01); *G06Q 30/04* (2013.01); *G16H 10/60* (2018.01); *G16H 40/20* (2018.01)

(58) Field of Classification Search

None

See application file for complete search history.

(56) References Cited

U.S. PATENT DOCUMENTS

| | | |
|---|---|---|
| 5,644,778 A | 7/1997 | Burks et al. |
| 5,918,208 A | 6/1999 | Javitt |
| 6,067,522 A | 5/2000 | Warady et al. |
| 6,195,612 B1 | 2/2001 | Pack-Harris |
| 6,205,434 B1 | 3/2001 | Ryan et al. |
| 6,208,973 B1 | 3/2001 | Boyer et al. |
| 6,341,265 B1 | 1/2002 | Provost et al. |

(Continued)

OTHER PUBLICATIONS

Steve Sinovic, "Quiet revolution," May 1, 2017, Albuquerque Journal, pp. 1-3.

(Continued)

*Primary Examiner* — Schquita D Goodwin
*Assistant Examiner* — Ishrat Rashid
(74) *Attorney, Agent, or Firm* — Armstrong Teasdale LLP

(57) ABSTRACT

A multi-layer adaptive routing (MLAR) computing device including at least one processor in communication with at least one memory adaptively routes packet data within one or more networks. The MLAR device stores a custom group instance on a database, the instance includes a network of a plurality of service providers and a consultant comprised of a plurality of user groups. The MLAR device submits a query to the database based on a data request from a user. Data packets are created based on the database's response to the query, which are then divided, routed, and transmitted among a plurality of users within the custom group instance.

20 Claims, 19 Drawing Sheets

(56) References Cited

U.S. PATENT DOCUMENTS

| | | | | |
|---|---|---|---|---|
| 6,401,079 | B1 | 6/2002 | Kahn et al. | |
| 6,735,569 | B1 | 5/2004 | Wizig | |
| 6,915,265 | B1 | 7/2005 | Johnson | |
| 7,305,347 | B1 | 12/2007 | Joao | |
| 7,419,094 | B2 | 9/2008 | Grear et al. | |
| 7,493,266 | B2 | 2/2009 | Gupta | |
| 7,739,131 | B1 | 6/2010 | Luedtke | |
| 7,742,930 | B1 | 6/2010 | Calhoun, Jr. et al. | |
| 7,890,356 | B1 | 2/2011 | Drucker et al. | |
| 8,327,020 | B1 * | 12/2012 | Sarathi | G16H 40/20 709/239 |
| 8,364,498 | B2 | 1/2013 | Sohr et al. | |
| 8,396,796 | B1 | 3/2013 | Vu et al. | |
| 8,521,564 | B1 * | 8/2013 | Ciechanowski | G16H 15/00 345/650 |
| 8,527,292 | B1 * | 9/2013 | Ozden | G16H 70/60 705/30 |
| 8,756,075 | B1 * | 6/2014 | Sultan | G06Q 40/08 705/2 |
| 9,846,914 | B1 | 12/2017 | Murray et al. | |
| 10,311,412 | B1 | 6/2019 | Josephs et al. | |
| 10,586,019 | B1 | 3/2020 | Dowling et al. | |
| 2002/0055858 | A1 | 5/2002 | Jackson | |
| 2002/0062224 | A1 | 5/2002 | Thorsen et al. | |
| 2002/0077869 | A1 | 6/2002 | Doyle et al. | |
| 2002/0103680 | A1 | 8/2002 | Newman | |
| 2002/0133459 | A1 | 9/2002 | Polk et al. | |
| 2003/0009355 | A1 * | 1/2003 | Gupta | G06Q 10/10 705/2 |
| 2003/0125987 | A1 | 7/2003 | Rucker | |
| 2003/0195769 | A1 | 10/2003 | Francis | |
| 2004/0039604 | A1 | 2/2004 | Tallal, Jr. | |
| 2004/0073460 | A1 | 4/2004 | Erwin | |
| 2004/0078234 | A1 | 4/2004 | Tallal, Jr. | |
| 2004/0078235 | A1 | 4/2004 | Tallal, Jr. | |
| 2005/0010436 | A1 | 1/2005 | Merkin | |
| 2005/0033604 | A1 | 2/2005 | Hogan | |
| 2005/0086075 | A1 | 4/2005 | Kaehler et al. | |
| 2005/0251428 | A1 | 11/2005 | Dust et al. | |
| 2005/0288968 | A1 | 12/2005 | Collins | |
| 2006/0053033 | A1 | 3/2006 | Wood | |
| 2006/0080144 | A1 | 4/2006 | Goel et al. | |
| 2006/0085230 | A1 | 4/2006 | Brill et al. | |
| 2007/0050219 | A1 | 3/2007 | Sohr et al. | |
| 2007/0106607 | A1 | 5/2007 | Seib et al. | |
| 2007/0130037 | A1 | 6/2007 | Miller | |
| 2007/0156551 | A1 | 7/2007 | Smith et al. | |
| 2007/0162307 | A1 | 7/2007 | Austin et al. | |
| 2007/0168234 | A1 | 7/2007 | Rutkowski et al. | |
| 2007/0179813 | A1 | 8/2007 | Darling | |
| 2007/0276695 | A1 * | 11/2007 | Lieberman | G06Q 10/10 705/40 |
| 2008/0010096 | A1 | 1/2008 | Patterson et al. | |
| 2008/0040155 | A1 | 2/2008 | Ray et al. | |
| 2008/0059251 | A1 | 3/2008 | Biorge | |
| 2008/0086325 | A1 | 4/2008 | James | |
| 2008/0208638 | A1 | 8/2008 | Davidson et al. | |
| 2009/0055224 | A1 | 2/2009 | Kashyap et al. | |
| 2009/0089085 | A1 | 4/2009 | Schoenberg | |
| 2009/0094065 | A1 | 4/2009 | Hyde et al. | |
| 2009/0132295 | A1 | 5/2009 | Pecan et al. | |
| 2009/0164242 | A1 | 6/2009 | Zubak et al. | |
| 2009/0171854 | A1 | 7/2009 | Joseph et al. | |
| 2009/0204441 | A1 | 8/2009 | Read et al. | |
| 2009/0326987 | A1 | 12/2009 | Roudaut | |
| 2010/0106518 | A1 * | 4/2010 | Kuo | G06Q 10/10 705/2 |
| 2010/0241458 | A1 | 9/2010 | Hasan et al. | |
| 2011/0106554 | A1 | 5/2011 | Benja-Athon | |
| 2011/0173019 | A1 | 7/2011 | Benja-Athon | |
| 2011/0320224 | A1 | 12/2011 | Sen et al. | |
| 2012/0239417 | A1 | 9/2012 | Pourfallah et al. | |
| 2012/0239560 | A1 | 9/2012 | Pourfallah et al. | |
| 2013/0110533 | A1 | 5/2013 | Paul et al. | |
| 2013/0110539 | A1 | 5/2013 | Sohr et al. | |
| 2013/0191136 | A1 | 7/2013 | Apshago et al. | |
| 2013/0226750 | A1 | 8/2013 | Friedholm et al. | |
| 2013/0226751 | A1 | 8/2013 | Friedholm et al. | |
| 2013/0311389 | A1 | 11/2013 | Kaehler et al. | |
| 2014/0095195 | A1 * | 4/2014 | Davis | G06Q 40/08 705/2 |
| 2014/0114674 | A1 | 4/2014 | Krughoff et al. | |
| 2014/0195265 | A1 | 7/2014 | Kings et al. | |
| 2014/0372133 | A1 | 12/2014 | Austrum et al. | |
| 2014/0379361 | A1 | 12/2014 | Mahadkar et al. | |
| 2015/0046188 | A1 | 2/2015 | De La Garza | |
| 2015/0051915 | A1 | 2/2015 | Moore | |
| 2015/0235313 | A1 | 8/2015 | Jiang | |
| 2015/0294338 | A1 | 10/2015 | Ketchel, III et al. | |
| 2015/0356513 | A1 | 12/2015 | Walkingshaw et al. | |
| 2016/0019357 | A1 | 1/2016 | Marzula et al. | |
| 2016/0085926 | A1 | 3/2016 | Ivanoff et al. | |
| 2016/0217261 | A1 | 7/2016 | Tuthill et al. | |
| 2016/0239614 | A1 * | 8/2016 | Siva | G06F 16/24575 |
| 2017/0053075 | A1 | 2/2017 | Moses et al. | |
| 2017/0177808 | A1 | 6/2017 | Irwin et al. | |
| 2017/0185723 | A1 | 6/2017 | McCallum et al. | |
| 2018/0047120 | A1 * | 2/2018 | Mathis | G06Q 50/22 |
| 2018/0048674 | A1 | 2/2018 | Black et al. | |
| 2018/0218348 | A1 | 8/2018 | Boyer et al. | |
| 2019/0188798 | A1 | 6/2019 | Foreman | |
| 2019/0318431 | A1 * | 10/2019 | Niemeyer | G16H 10/60 |

OTHER PUBLICATIONS

Nora Doyle-Burr, "Frustration Drives Direct Care Efforts," Nov. 19, 2017, Valley News [White River Junction, VI], pp. 1-5.

Matt Goodman, "Live Free Or Die," Matt Goodman, Apr. 2016, D-Dallas/Fort Worth 43:4: D Magazine, pp. 1-5.

PR Newswire, "Ameriflex regoranizes executive team to support sister company Accresa, drive innovation in benefits payment technology," Jan. 3, 2018, PR Newsire [New York], pp. 1-3.

PR Newswire, "Ameriflex celebrates 20 years of helping American families pay for health care," Mar. 1, 2018, PR Newswire [New York], pp. 1-3.

* cited by examiner

1400B

SYSTEMS AND METHODS FOR MULTI-LAYER ADAPTIVE PACKET ROUTING

CROSS REFERENCE TO RELATED APPLICATIONS

This application is a continuation-in-part of U.S. Non-Provisional application Ser. No. 16/449,111, filed Jun. 21, 2019, which is a continuation of U.S. Non-Provisional application Ser. No. 16/018,524, filed Jun. 26, 2018, the contents of which are hereby incorporated by reference in their entirety.

BACKGROUND

The field of the invention relates generally to multi-layer adaptive routing of packet data, and more specifically to systems and methods for adaptively routing data packets on a network in a secure and efficient manner.

In many cases, a business, or employer, allocates a portion of business funds to one or more healthcare plans for their employees. The plans then provide financial payment to appropriate healthcare providers based on services provided to the employees. In other cases, the employer self-funds the healthcare plan and pays the healthcare providers and/or plan coordinators for the services provided. These methods may generate a lot of risk for the employer, as the number and cost of visits to healthcare providers by employees may vary. This variability makes budgeting and cost forecasting cumbersome. Furthermore, the billing for services rendered model used by the prior art for healthcare providers is inefficient. For example, a typical healthcare provider may have to bill for each individual visit and individually receive payment for each visit, thereby causing high overhead and undue stress on a payment network.

BRIEF DESCRIPTION

The present embodiments may relate to, inter alia, systems and methods for multi-layer adaptive routing of packet data. In one aspect, a system is leveraged for the routing of packet data within a network in response to a single event. In some exemplary embodiments, the system includes a computer system including at least one processor in communication with a memory.

In a first aspect, a multi-layer adaptive routing (MLAR) computing device comprising at least one processor in communication with a memory device may be provided. The at least one processor may be configured to: 1) store, on a database, a custom group instance including a network of a plurality of service providers and a consultant including a plurality of user groups, 2) receive a data request from at least one of a plurality of users of one of the plurality of user groups of the custom group instance, 3) submit a query to the database based at least in part on the data request, 4) create, based on a response from the database based on the query, data packets and divide and route the data packets among at least some of plurality of users within the custom group instance, and 5) transmit the divided data packets to the at least some of the plurality of users. The MLAR computing device may include additional, less, or alternate functionality including that discussed elsewhere herein.

In another aspect, a method for multi-layer adaptive routing of data packets is provided. The computer implemented method may include: 1) storing, on a database, a custom group instance including a network of a plurality of service providers and a consultant including a plurality of user groups, 2) receiving a data request from at least one of a plurality of users of one of the plurality of user groups of the custom group instance, 3) submitting a query to the database based at least in part on the data request, 4) creating, based on a response from the database based on the query, data packets and divide and route the data packets among at least some of plurality of users within the custom group instance, and 5) transmitting the divided data packets to the at least some of the plurality of users. The method may include additional, less, or alternate steps, including that discussed elsewhere herein.

In yet another aspect, a non-transitory computer-readable media having computer-executable instructions embodied thereon is provided. The instructions, when executed by a multi-layer adaptive routing (MLAR) computing device including at least one processor in communication with a memory device cause the at least one processor to: 1) store, on a database, a custom group instance including a network of a plurality of service providers and a consultant including a plurality of user groups, 2) receive a data request from at least one of a plurality of users of one of the plurality of user groups of the custom group instance, 3) submit a query to the database based at least in part on the data request, 4) create, based on a response from the database based on the query, data packets and divide and route the data packets among at least some of plurality of users within the custom group instance, and 5) transmit the divided data packets to the at least some of the plurality of users. The instructions may cause additional, less, or alternative functionality, including that discussed elsewhere herein.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the systems and methods disclosed therein. Each Figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and are instrumentalities shown, wherein.

DETAILED DESCRIPTION

Foundational Paragraphs

The present embodiments may relate to, inter alia, systems and methods for leveraging a computing system in response to a single event to adaptively route data packets within a network. More specifically, in response to a single event, a computing system is leveraged for the dynamic routing of packet data among a plurality of devices connected via one or more networks. In one exemplary embodiment, the process may be performed by a multi-layer adaptive routing (MLAR) computing device. In the exemplary embodiment, the MLAR computing device is in communication with a plurality of user computer devices and a plurality of provider computer devices.

In an exemplary embodiment, the MLAR computer device receives user information from computer devices associated with a plurality of administrators. The MLAR computer device also receives participant information from a plurality of providers. The participant information, for example, includes information about which user of the plurality of user that are associated with each of the plurality of providers.

In an exemplary embodiment, the MLAR computer device receives employee information from computer devices associated with a plurality of employers. The MLAR computer device also receives patient information from a plurality of healthcare providers. The patient information includes at least information about which employees of the plurality of employees that are associated with each of the plurality of healthcare providers. The MLAR computer device receives payments from the employers for the healthcare providers. The MLAR computer device divides each payment from an employer into segments based on the employees associated with that employer. The MLAR computer device uses the patient information to determine which employees are associated with each healthcare provider and generates a payment based on that payment. In some embodiments, the MLAR computer device divides the payment equally, providing the same amount to each healthcare provider per the number of employees that are associated with that healthcare provider. In other embodiments, the MLAR computer device divides the payments by multiple criteria, such as, but not limited to a healthcare plan associated with the corresponding employee, a number of covered family members of the corresponding employee, and an employment category associated with the corresponding employee. In some embodiments, different employers pay different amounts per employee and the MLAR computer device divides the payment based on the employer associated with the payment. In some embodiments, different providers charge different amounts per employee and the MLAR computer device adjusts the payment to the healthcare provider appropriately.

Exemplary System for Multi-Layer Adaptive Packet Routing

Figure 1:
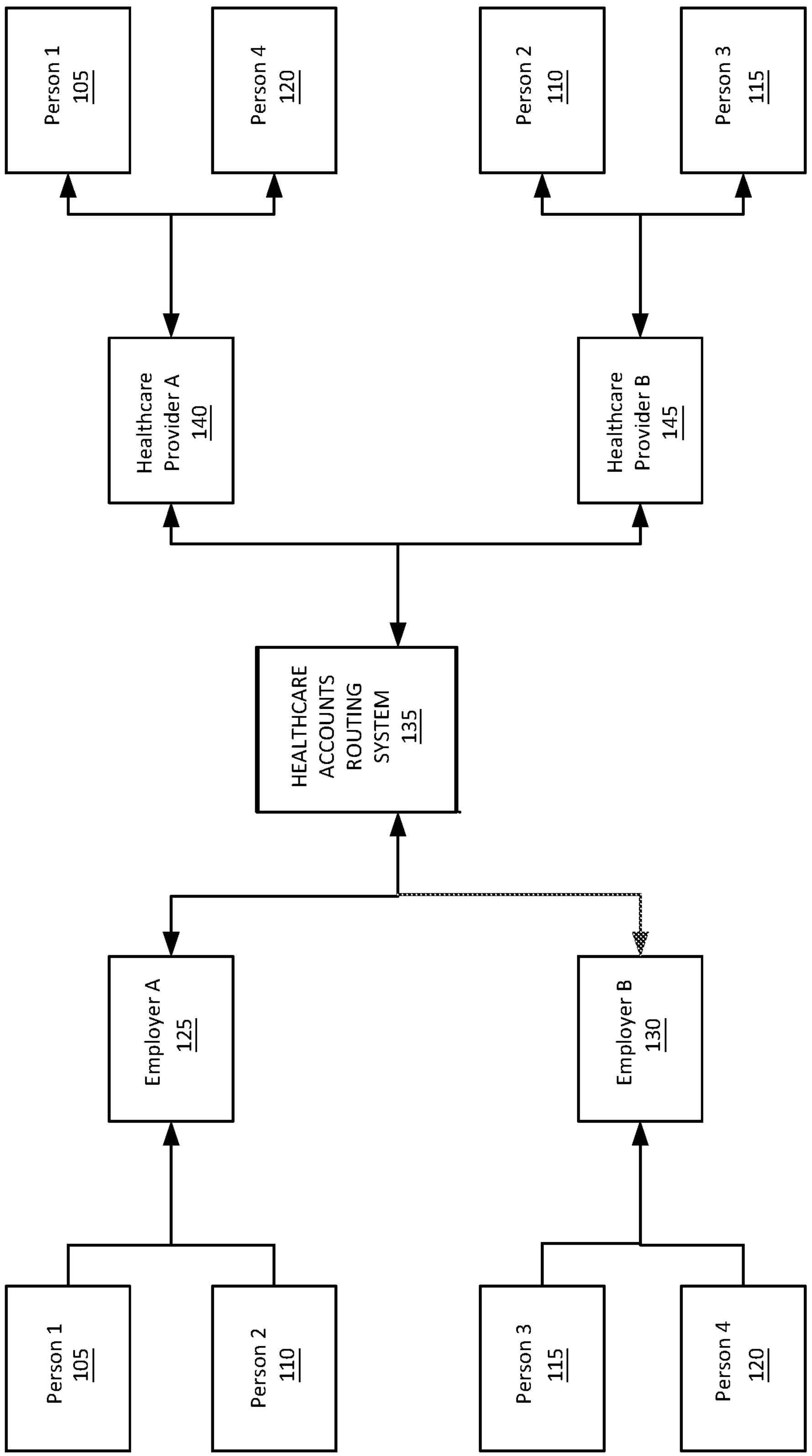
FIG. 1 illustrates a simplified data flow diagram of routing multi-layer adaptive data and information in accordance with one embodiment of the disclosure.

FIG. 1 illustrates a simplified data flow diagram of routing multi-layer adaptive payments and information in accordance with one embodiment of the disclosure. In the exemplary embodiment, a plurality of employees works for a plurality of employers. As shown in FIG. 1, persons A 105 and B 110 work for employer A 125. Persons C 115 and D 120 work for employer B 130. In the exemplary embodiment, there are a plurality of employers that each are associated with a plurality of employees.

The employers 125 and 130 provide healthcare coverage to their employees. Each of the employees may visit different healthcare providers, such as persons A 105 and D 120 visiting healthcare provider A 140 and persons B 110 and C 115 visiting healthcare provider B 145. In the exemplary embodiment, a healthcare provider 140 & 145 may include, but is not limited to, a healthcare clinic, a hospital, a primary care physician, an urgent care clinic, and a specialist doctor.

In the exemplary embodiment, employer A 125 transmits information about person A 105 and person B 110 to the MLAR system 135. The information includes at least the indication that person A 105 and person B 110 are employed by employer A 125 and are covered for healthcare by employer A 125. Other information could include, but is not limited to, a healthcare plan associated with the corresponding employee, a number of covered family members of the corresponding employee, and an employment category associated with the corresponding employee.

Employer A 125 also transmits a payment to MLAR system 135 to cover healthcare services for person A 105 and person B 110. MLAR system 135 divides that payment into sub-payments based on the information about person A 105 and person B 110. In some embodiments, the division is even, where the sub-payment for each person is the same amount. In other embodiments, the division is based on one or more factors, such as those in the information provided by employer A 125. For example, the sub-payments may be divided up based on the number of covered people in person A's family and the number of covered people in person B's family.

Healthcare providers A 140 and B 145 transmit patient information to MLAR system 135. In some embodiments, the patient information just includes the indication that person A 105 and person D 120 are associated with healthcare provider A 140. In other embodiments, the patient information may include additional information, such as, but not limited to, how many visits each person has made in a predetermined period of time and other information that may be limited by healthcare data privacy laws.

MLAR system 135 uses the patient information and the information provided by the employers to determine how much each healthcare provider is owed. In the example shown in FIG. 1, MLAR system 135 takes the sub-payment associated with person A 105 and the sub-payment associated with person D 120, combines the two payments, and transmits the combined payment to healthcare provider A 140. MLAR system 135 then takes the sub-payment associated with person B 110 and the sub-payment associated with person C 115, combines the two payments, and transmits the combined payment to healthcare provider B 145. By combining all of the payments for all of the individuals seen by the healthcare provider, the present system reduces the payment message traffic required and further reduces the paperwork and computer resources needed to bill for and process payments to healthcare providers.

In some embodiments, the MLAR system 135 transmits a payment to each healthcare provider 140 and 145 every month. In some further embodiments, the healthcare providers 140 and 145 provide services for individuals based on a monthly fee instead of charging for each service received.

In some embodiments, MLAR system 135 requests and/or receives data from the employers 125 & 130 and from the healthcare providers 140 & 145. The MLAR system 135 uses the received data to update its stored data. In some embodiments, the MLAR system 135 compares the received data to the stored data to determine changes and updates to the stored data. For example, MLAR system 135 may have stored data saying that person A 105 is associated with healthcare provider A 140. Then MLAR system 135 may receive data from healthcare provider B 145 stating that person A 105 is associated with healthcare provider B 145. In these embodiments, the MLAR system 135 may request updated data from healthcare provider A 140 to determine whether person A 105 is still associated with healthcare provider A 140.

FIG. 1 only shows two employers 125 & 130 with only two employees each and only two healthcare providers 140 & 145. These limited quantities are for illustrative purposes only. In the exemplary embodiment, the MLAR system 135 is configured to handle significantly greater numbers of employees, employers, and healthcare providers. For example, the MLAR system 135 may work with fifty employers each with between 50 and 500 employees. Furthermore, the employees may visit several hundred different healthcare providers overall. These numbers are for illustration purposes only as the MLAR system 135 can handle many different combinations of numbers.

Exemplary Multi-Layer Adaptive Routing System

Figure 2:
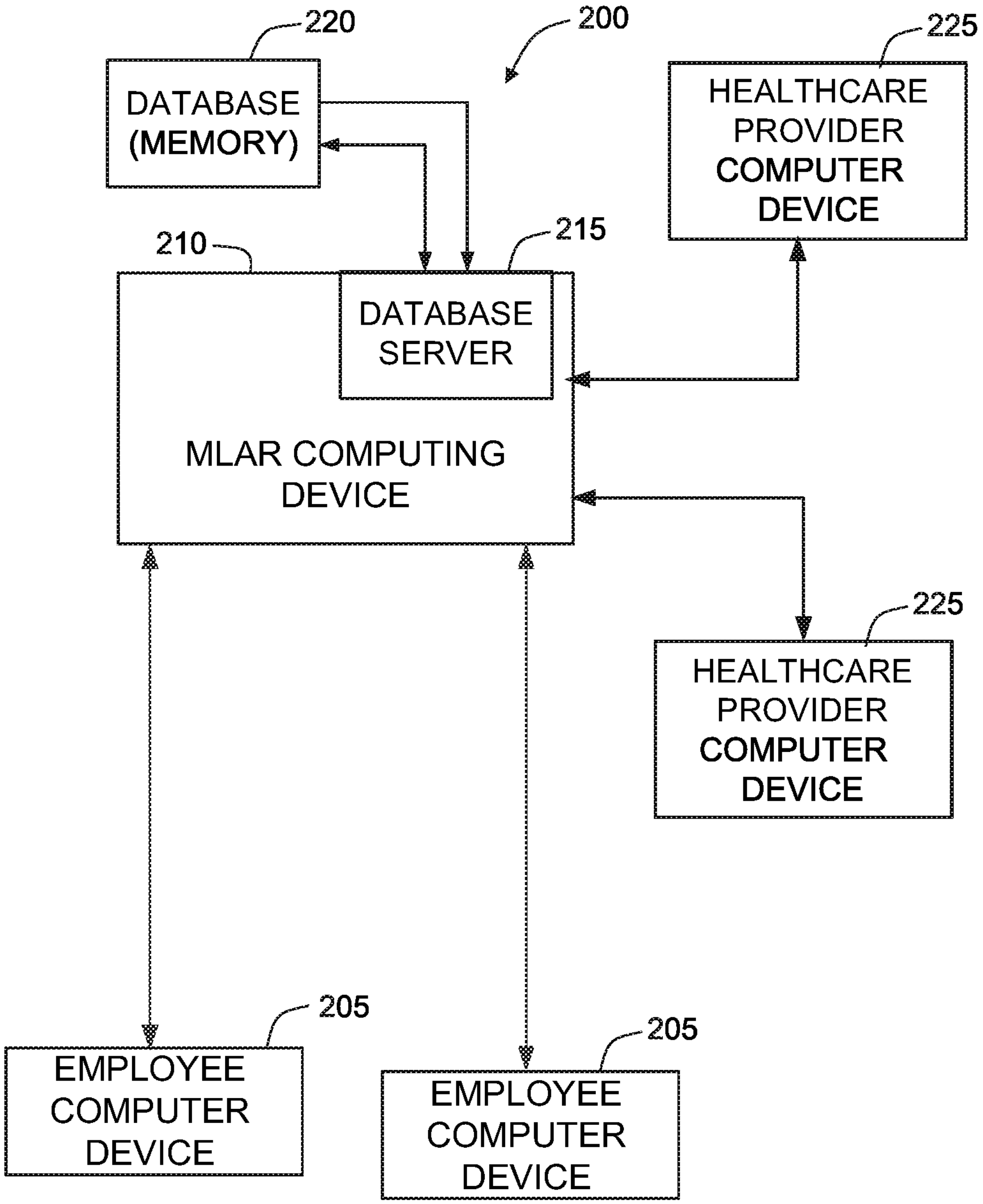
FIG. 2 illustrates a simplified block diagram of an exemplary multi-layer adaptive routing system for dynamically routing data packets and other information.

FIG. 2 illustrates a simplified block diagram of an exemplary multi-layer adaptive routing system 200 for dynamically routing multi-layer adaptive payments and information. As described below in more detail, a multi-layer adaptive routing ("MLAR") server 210 (also known as a MLAR computer device 210), may be configured to (i) store a first plurality of data associated with an employer including a plurality of employees associated with the employer; (ii) receive a payment from the employer; (iii) divide the payment into a plurality of sub-payments based on the plurality of employees; (iv) storing a second plurality of data associated with a plurality of healthcare providers, wherein each healthcare provider of the plurality of healthcare providers is associated with one or more employees of the plurality of employees; (v) for each healthcare provider of the plurality of healthcare providers, determining a healthcare payment based on the associated one of more employees and the plurality of sub-payments; and (vi) for each healthcare provider, routing the healthcare payment to the corresponding healthcare provider as described herein.

In another embodiment, and as described below in more detail, the MLAR server may be configured to (i) store, on a database, a custom group instance including a network of a plurality of service providers and a consultant including a plurality of user groups, (ii) receive a data request from at least one of a plurality of users of one of the plurality of user groups of the custom group instance, (iii) submit a query to the database based at least in part on the data request, (iv) create, based on a response from the database based on the query, data packets and divide and route the data packets among at least some of plurality of users within the custom group instance, and (v) transmit the divided data packets to the at least some of the plurality of users. as described herein.

In yet another embodiment, and as described below in more detail, the MLAR server may be configured to (i) provide user access to the system, such as via a graphical user interface (GUI), or the like, (ii) perform authentication of the user attempting to access system, (iii) provide, via the GUI, system access allowing user to interact with system and perform actions (e.g., registration, modification, enrollment, etc.), (iv) create data packets based on the user's performed actions, (v) divide and route the created data packets among relevant user's of the system, such as to their associated user devices, and (vi) transmit the divided data packets to the relevant users via a network.

In the exemplary embodiment, employer computer devices 205 are computers that include a web browser or a software application, which enables employer computer devices 205 to access remote computer devices, such as MLAR server 210, using the Internet or other network. More specifically, employer computer devices 205 may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. Employer computer devices 205 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices. In the exemplary embodiment, employer computer devices 205 are associated with employers, such as Employer A 125 and Employer B 130 (both shown in FIG. 1).

In the exemplary embodiment, healthcare provider computer devices 225 are computers that include a web browser or a software application, which enables healthcare provider computer devices 225 to access remote computer devices, such as MLAR server 210, using the Internet or other network. More specifically, healthcare provider computer devices 225 may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. Healthcare provider computer devices 225 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices. In the exemplary embodiment, healthcare provider computer devices 225 are associated with healthcare providers, such as healthcare provider A 140 and healthcare provider B 145 (both shown in FIG. 1).

A database server 215 is communicatively coupled to a database 220 that stores data. In one embodiment, database 220 may include employer data, employee information, payment information, and patient information. In the exemplary embodiment, database 220 is stored remotely from MLAR server 210. In some embodiments, database 220 is decentralized. In the exemplary embodiment, a user may access database 220 via a user computer device, such as employer computer device 205 and healthcare provider computer device 225, by logging onto MLAR server 210, as described herein.

In the exemplary embodiment, MLAR server 210 may be similar to MLAR system 135 (shown in FIG. 1). MLAR server 210 may be in communication with a plurality of employer computer devices 205 and healthcare provider computer devices 225 to route multi-layer adaptive payments and information. More specifically, MLAR server 210 may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular phone connection, and a cable modem. MLAR server 210 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices. In some embodiments, MLAR server 210 is also associated with a plurality of user computer device (not shown) that allow individual users to access MLAR server 210 and database 220. In some embodiments, MLAR server 210 comprises a plurality of computer devices working in concert.

Exemplary Client Computing Device

Figure 3:
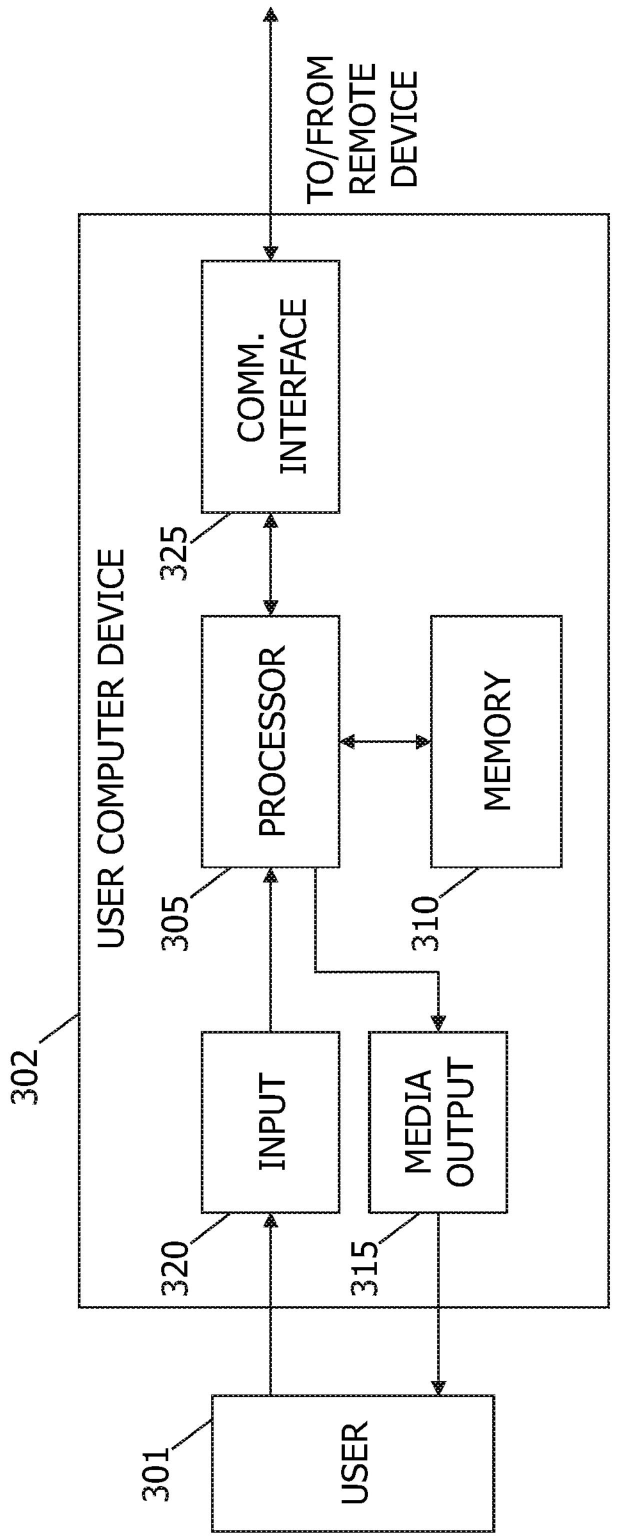
FIG. 3 illustrates an exemplary configuration of a client computer device as shown in FIG. 2, in accordance with one embodiment of the present disclosure.

FIG. 3 depicts an exemplary configuration of client computer device, in accordance with one embodiment of the present disclosure. User computer device 302 may be operated by a user 301. User computer device 302 may include, but is not limited to, employer computer devices 205 and healthcare provider computer devices 225 (both shown in FIG. 5). User computer device 302 may include a processor 305 for executing instructions. In some embodiments, executable instructions may be stored in a memory area 310. Processor 305 may include one or more processing units (e.g., in a multi-core configuration). Memory area 310 may be any device allowing information such as executable instructions and/or transaction data to be stored and retrieved. Memory area 310 may include one or more computer readable media.

User computer device 302 may also include at least one media output component 315 for presenting information to user 301. Media output component 315 may be any component capable of conveying information to user 301. In some embodiments, media output component 315 may include an output adapter (not shown) such as a video adapter and/or an audio adapter. An output adapter may be operatively coupled to processor 305 and operatively couplable to an output device such as a display device (e.g., a cathode ray tube (CRT), liquid crystal display (LCD), light emitting diode (LED) display, or "electronic ink" display) or an audio output device (e.g., a speaker or headphones).

In some embodiments, media output component 315 may be configured to present a graphical user interface (e.g., a web browser and/or a client application) to user 301. A graphical user interface may include, for example, an interface for viewing and editing accounts and account information. In some embodiments, user computer device 302 may include an input device 320 for receiving input from user 301. User 301 may use input device 320 to, without limitation, edit account information.

Input device 320 may include, for example, a keyboard, a pointing device, a mouse, a stylus, a touch sensitive panel (e.g., a touch pad or a touch screen), a gyroscope, an accelerometer, a position detector, a biometric input device, and/or an audio input device. A single component such as a touch screen may function as both an output device of media output component 315 and input device 320.

User computer device 302 may also include a communication interface 325, communicatively coupled to a remote device such as MLAR server 210 (shown in FIG. 2). Communication interface 325 may include, for example, a wired or wireless network adapter and/or a wireless data transceiver for use with a mobile telecommunications network.

Stored in memory area 310 are, for example, computer readable instructions for providing a user interface to user 301 via media output component 315 and, optionally, receiving and processing input from input device 320. A user interface may include, among other possibilities, a web browser and/or a client application. Web browsers enable users, such as user 301, to display and interact with media and other information typically embedded on a web page or a website from MLAR server 210. A client application may allow user 301 to interact with, for example, MLAR server 210. For example, instructions may be stored by a cloud service, and the output of the execution of the instructions sent to the media output component 315.

Exemplary Server Computing Device

Figure 4:
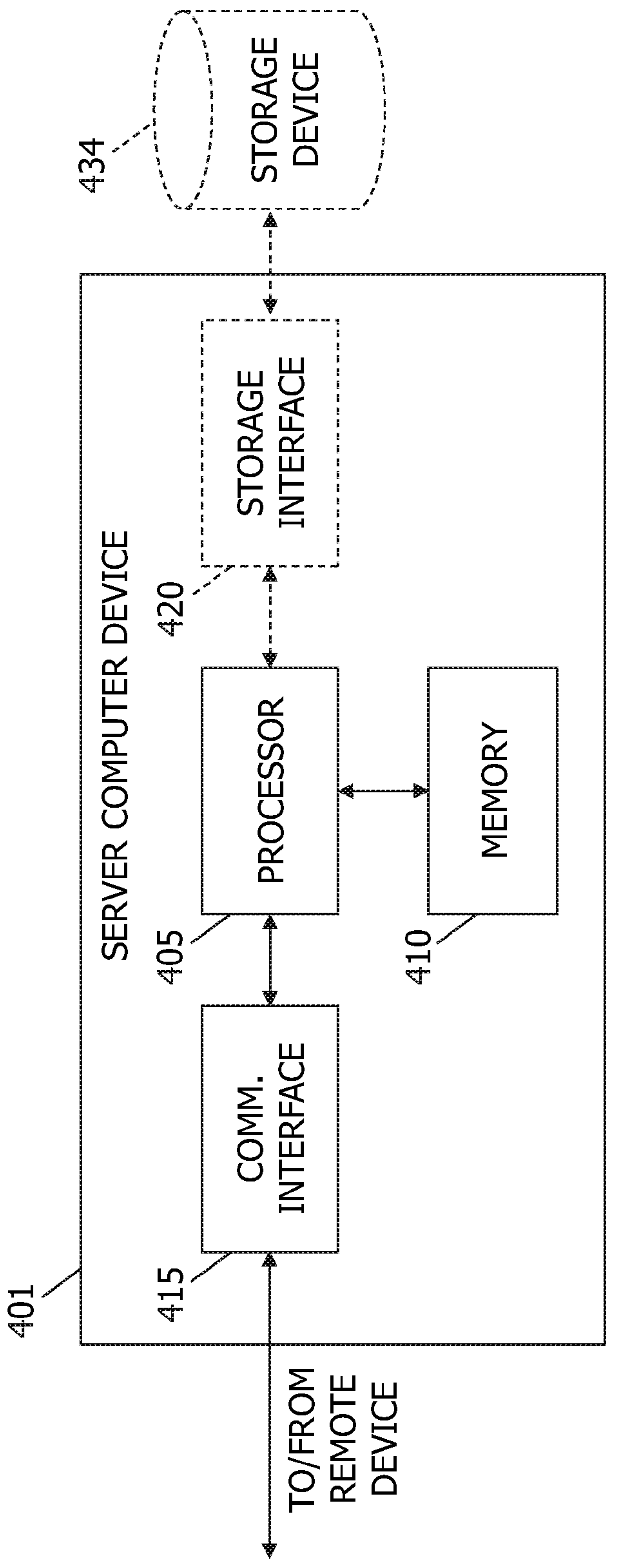
FIG. 4 illustrates an exemplary configuration of a server system as shown in FIG. 2, in accordance with one embodiment of the present disclosure.

FIG. 4 depicts an exemplary configuration of server system, in accordance with one embodiment of the present disclosure. Server computer device 401 may include, but is not limited to, employer computer device 205, MLAR server 210, database server 215, and healthcare provider computer device 225 (all shown in FIG. 2). Server computer device 401 may also include a processor 405 for executing instructions. Instructions may be stored in a memory area 410. Processor 405 may include one or more processing units (e.g., in a multi-core configuration).

Processor 405 may be operatively coupled to a communication interface 415 such that server computer device 401 is capable of communicating with a remote device such as another server computer device 401, MLAR server 210, employer computer device 205, and healthcare provider computer device 225 (for example, using wireless communication or data transmission over one or more radio links or digital communication channels). For example, communication interface 415 may receive requests from employer computer devices 205 and healthcare provider computer devices 225 via the Internet, as illustrated in FIG. 2.

Processor 405 may also be operatively coupled to a storage device 434. Storage device 434 may be any computer-operated hardware suitable for storing and/or retrieving data, such as, but not limited to, data associated with database 220 (shown in FIG. 2). In some embodiments, storage device 434 may be integrated in server computer device 401. For example, server computer device 401 may include one or more hard disk drives as storage device 434.

In other embodiments, storage device 434 may be external to server computer device 401 and may be accessed by a plurality of server computer devices 401. For example, storage device 434 may include a storage area network (SAN), a network attached storage (NAS) system, and/or multiple storage units such as hard disks and/or solid state disks in a redundant array of inexpensive disks (RAID) configuration.

In some embodiments, processor 405 may be operatively coupled to storage device 434 via a storage interface 420. Storage interface 420 may be any component capable of providing processor 405 with access to storage device 434. Storage interface 420 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 405 with access to storage device 434.

Processor 405 may execute computer-executable instructions for implementing aspects of the disclosure. In some embodiments, the processor 405 may be transformed into a special purpose microprocessor by executing computer-executable instructions or by otherwise being programmed. For example, the processor 405 may be programmed with the instructions.

Routing Multi-Layer Adaptive Payments

Figure 5:
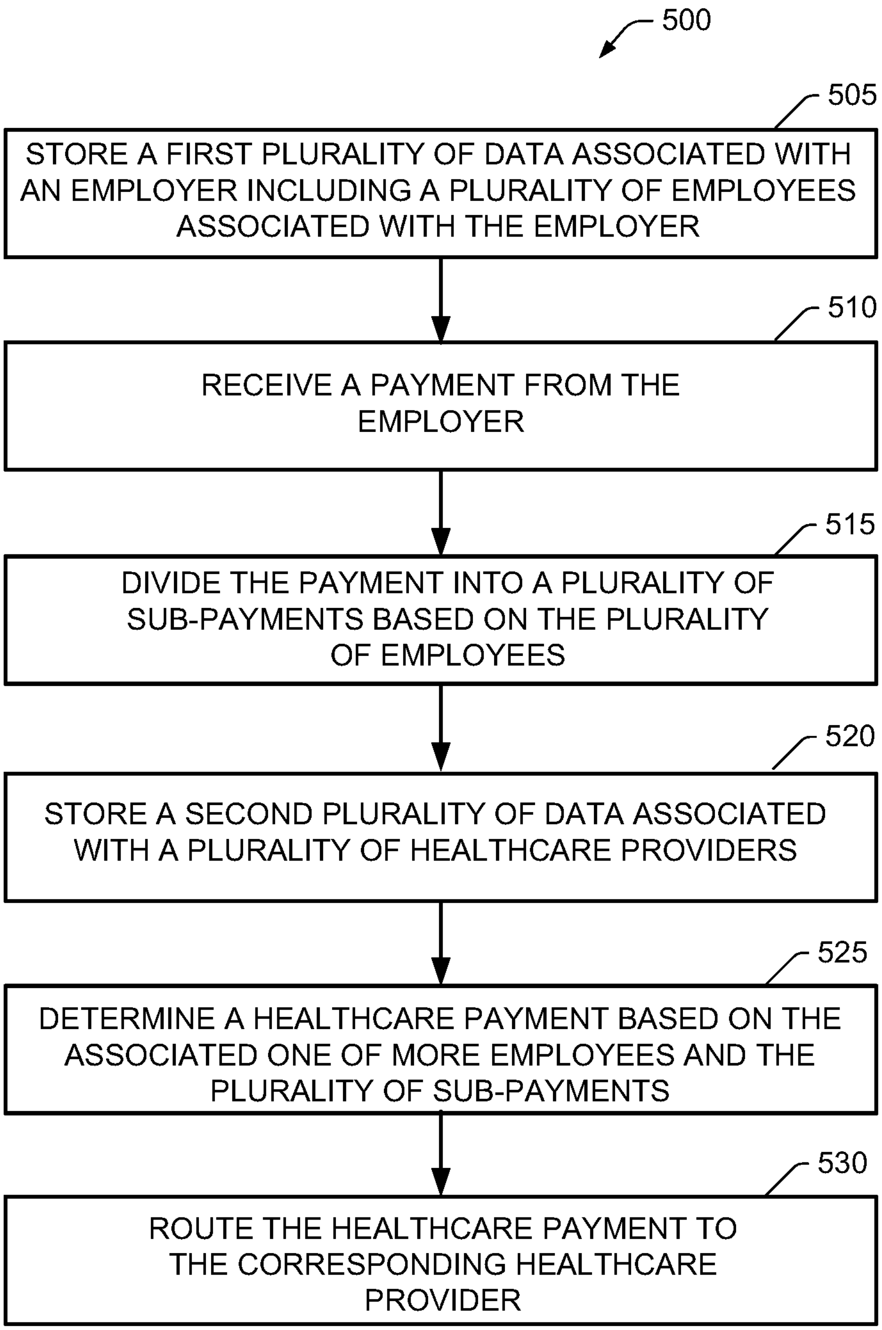
FIG. 5 illustrates a process for routing multi-layer adaptive payments in accordance with one embodiment of the disclosure.

FIG. 5 illustrates a process 500 for routing multi-layer adaptive payments in accordance with one embodiment of the disclosure. In the exemplary embodiment, process 500 is performed by MLAR server 210 (shown in FIG. 2). In other embodiments, process 500 is performed by a plurality of computer devices.

In the exemplary embodiment, MLAR server 210 stores 505 a first plurality of data associated with an employer, such as employer A 125 (shown in FIG. 1), including a plurality of employees associated with the employer 125. MLAR server 210 receives 510 a payment from the employer 125. In one embodiment, MLAR server 210 stores the payment in one or more escrow accounts.

In the exemplary embodiment, MLAR server 210 divides 515 the payment into a plurality of sub-payments based on the plurality of employees. In some embodiments, MLAR server 210 divides 515 the payment into even sub-payments based on a number of the plurality of employees. In other embodiments, MLAR server 210 divides 515 the payment into sub-payments based on one or more of a healthcare plan associated with the corresponding employee, a number of covered family members of the corresponding employee, and an employment category associated with the corresponding employee.

In the exemplary embodiment, MLAR server 210 stores 520 a second plurality of data associated with a plurality of healthcare providers, such as healthcare provider A 140 and healthcare provider B 145 (both shown in FIG. 1). Each healthcare provider of the plurality of healthcare providers is associated with one or more employees of the plurality of employees, where the employees use the corresponding healthcare provider to receive medical care.

For each healthcare provider of the plurality of healthcare providers, MLAR server 210 determines 525 a healthcare payment for the corresponding healthcare provider based on the associated one of more employees and the plurality of sub-payments. In some embodiments, MLAR server 210 determines 525 the healthcare payment based on a number of family members of employees associated with the corresponding healthcare provider. For example, in a family with five covered members, three members of the family may use healthcare provider A 140 and the other two use healthcare provider B 145. The portion of the employer's payment that is provided to each healthcare provider based on the family members is based on one or more rules set by the employer and/or the healthcare plan that the employee is associated with.

For each healthcare provider, MLAR server 210 routes 530 the healthcare payment to the corresponding healthcare provider. In the exemplary embodiment, MLAR server 210 instructs a computer device associated with the escrow account to route the healthcare payment to an account associated with the corresponding healthcare provider. In some embodiments, MLAR server 210 transmits the plurality of healthcare payments monthly.

In some further embodiments, the sub-payment associated with each employee is applied to the associated healthcare provider independent of whether the corresponding employee visited the corresponding healthcare provider.

In some embodiments, one or more employees of the plurality of employees are associated with more than one healthcare provider. In the embodiments, MLAR server 210 divides 515 the sub-payments for one of the one or more employees between the healthcare providers associated with the employee.

In some embodiments, MLAR server 210 receives an updated list of employee data from the employer 125. MLAR server 210 updates the first plurality of data based on the updated list of employee data. In some other embodiments, MLAR server 210 receives an updated list of associated employees from the healthcare provider. MLAR server 210 updates the second plurality of data based on the updated list of associated employees.

Network and Consultant Instance and Affiliate Networks

Figure 6A:
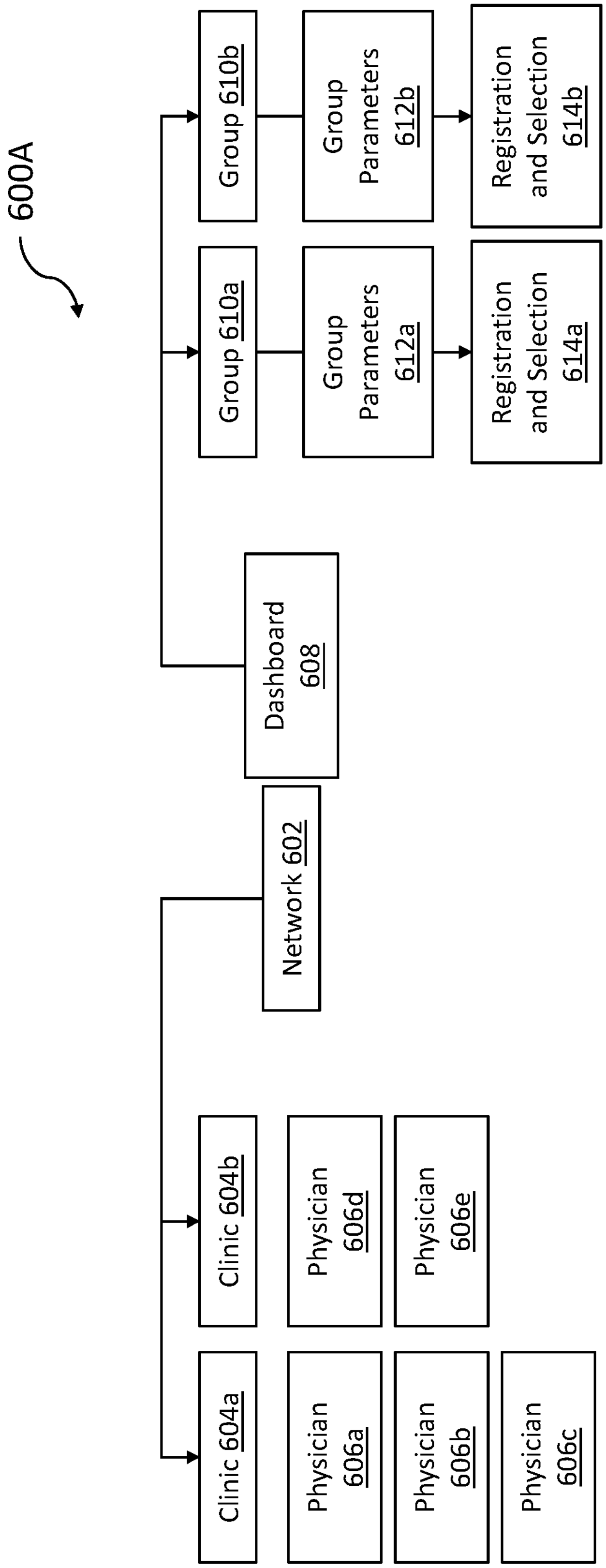
FIG. 6A illustrates an exemplary instance of a network and consultant in accordance with one embodiment of the present disclosure.

FIG. 6A depicts an exemplary configuration of a custom group instance 600A. The custom group instance 600A may include, but is not limited to, a network 602 and a dashboard device 608 in accordance with one embodiment of the present disclosure. While only one network node 602 and dashboard device 608 is illustrated for example purposes, one having skill in the art would understand that network node 602 may be a part of a cluster of network nodes 602 and the dashboard device 608 may be a part of a plurality of dashboard devices 608. In the exemplary embodiment, network 602 may be communicatively coupled to dashboard device 608 over a network. The dashboard device 608 may be used to administrate and maintain multiple groups, such as group 610*a* and group 610*b*, as illustrated, within a custom group instance. In some embodiments, the dashboard device 608 may be provided to allow for the management of custom group instances. For example, an employer may manage, via dashboard device 608, a group of employees that may be provided with access to a network of service providers in accordance with a custom group instance. Further, an employer may customize the group instance to include a sub-network of additional independent service providers, for example. Information pertaining to network 602 and dashboard device 608, may include, but is not limited to, network addresses or logical connections, or the like, which may be stored on a secure storage device, such as database 220 (shown in FIG. 2).

In some embodiments, each group of the custom group instance 600A, such as groups 610*a* and 610*b*, may include one or more unique parameters, such as group parameters 612*a* and 612*b*. In each instance of a group, unique parameters may include, but are not limited to, provider offerings (e.g., a sub-network), plans or services (e.g., global or custom to providers within a sub-network), consumer prices, consumer fees, and third-party payee information. The one or more unique parameters may be created, changed, or updated in response to user interactions with the system. A user may interact with the custom group instance 600A, for example, via a dashboard device 608. A user performing the interaction may include, but is not limited to, members, participants, providers, employees, employers, physicians, clinicians, and administrators associated with the custom group instance. For example, during a registration process, a group participant may provide sensitive personal data intended for a limited audience determined based on a plan subscribed to by the participant. In some embodiments, the plan may be customizable, including only a certain number of providers, and may include specific rules regarding who is permitted to access the information provided by the participant. Information pertaining to groups 610*a* and 610*b*, such as unique parameters 612*a* and 612*b*, and/or user registration and selection data 614*a* and 614*b*, may be stored on a secure storage device, such as database 220.

In some embodiments, a network 602 may be connected to a plurality of clinic devices, such as clinic device 604*a* or 604*b*. It is understood that the number of clinic devices within a network 602 is not meant to be limiting. Each clinic device 604*a* and 604*b* may organize and include a series of provider nodes, such as physician devices 606*a*-606*c* associated with clinic devices 604*a* and physician devices 606*d* and 606*e* associated with clinic device 604*b*. In some embodiments, any number of providers, such as physician devices 606*a*-606*c*, may be associated with, for example, independent physicians organized by a clinic device, such as clinic device 604*a*. Information pertaining to clinic devices 604*a* and 604*b* and the managed physician devices 606*a*-606*e*, may be stored on a secure storage device, such as database 220 (shown in FIG. 2).

Figure 6B:
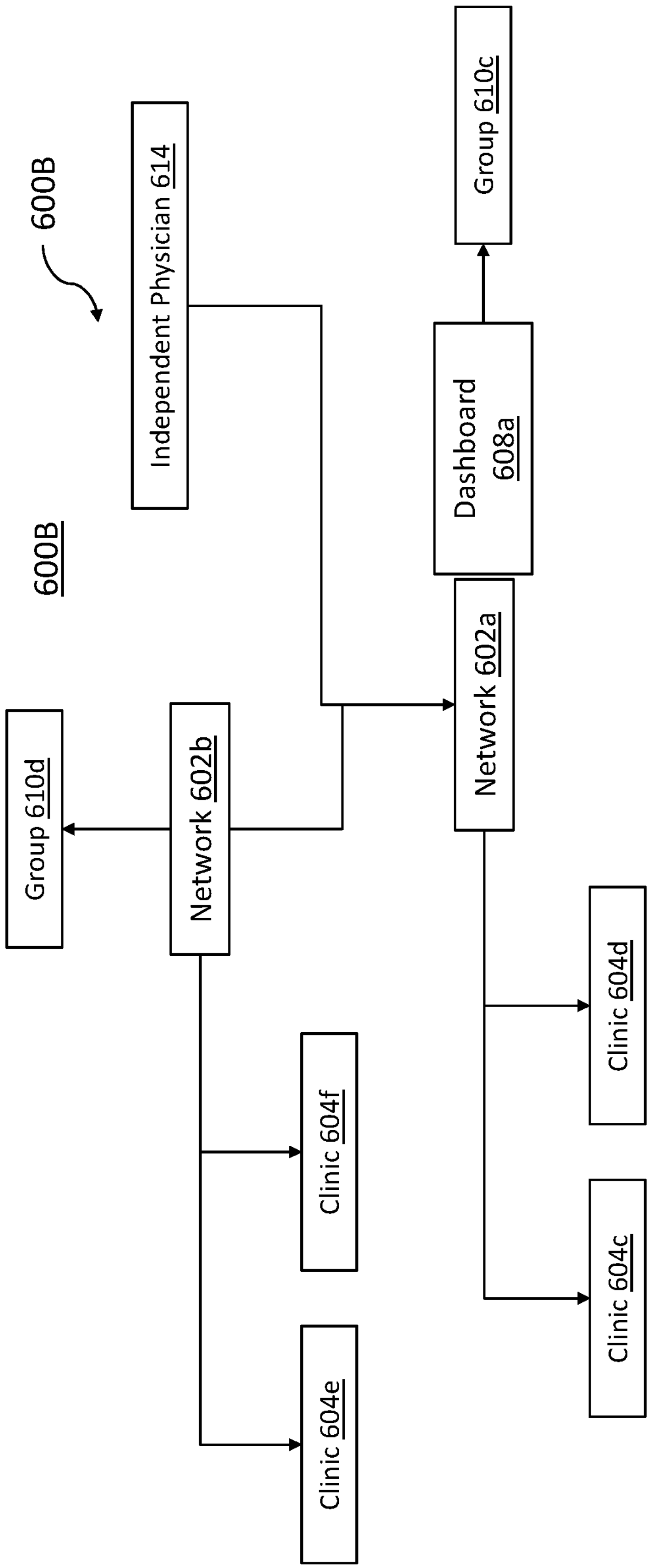
FIG. 6B illustrates another exemplary instance of a network and consultant in accordance with another embodiment of the present disclosure.

FIG. 6B depicts an exemplary configuration of an exemplary configuration 600B of an instance of a network 602A, a dashboard device 608, and an affiliate network node 602*b*, in accordance with one embodiment of the present disclosure. In this example, network 602*a* may be connected to an affiliate network node, network 602*b*. While only one affiliate network node is illustrated for example purposes, one having skill in the art would understand that affiliate network node 602*b* may be one of many affiliate network nodes. Affiliate network node 602*b* may be used to expand network coverage within an exemplary instance 600B. In some embodiments, affiliate network node 602*b* may be connected to a group 610*d*. Group 610*d* may include unique parameters pertaining to user registration and selection as described above in view of FIG. 6A. Additionally, or alternatively, group 610*d* may be connected to a plurality of clinic devices, such as clinic device 604*e* and clinic device 604*f*, for example. Further, network 602*b* may be connected to one or more physician devices, such as independent physician device 614. A physician device that is associated with an independent physician may not necessarily be associated with a certain group. Instead, independent physician device 614 may connected directly to a network node, such as network 602*f*. By being connected to network 602*f*, an independent physician of physician device 614 may expand their accessibility, such as to users of groups 610*c* or 610*d*, for example. Information pertaining to affiliate network 602*b*, group 610*d* and clinic devices 604*e* and 604*f* may be stored on a secure storage device, such as database 220 (shown in FIG. 2).

Figure 7A:
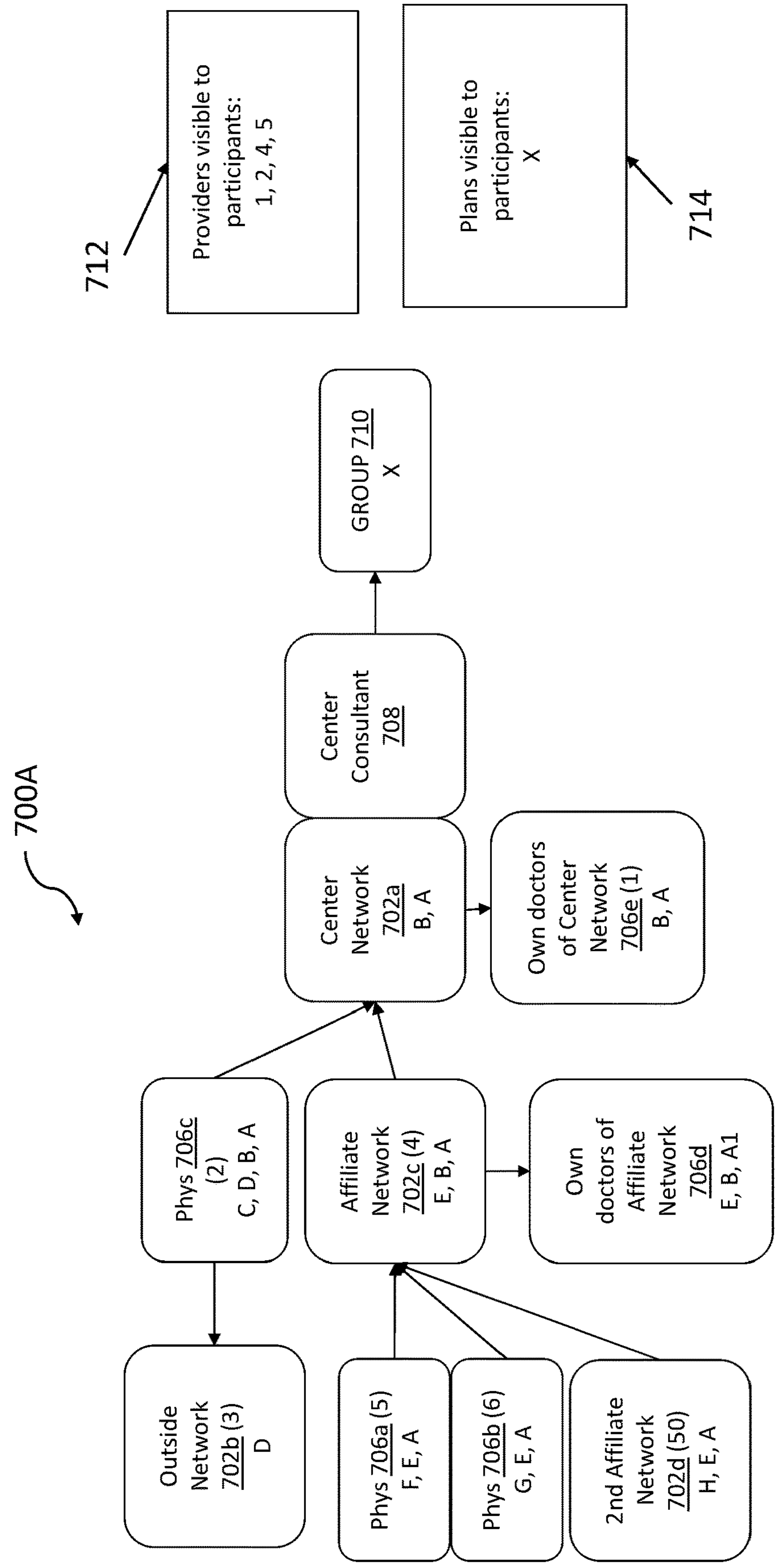
FIGS. 7A-7C illustrate exemplary network affiliations in accordance with embodiments of the present disclosure.
Figure 7B:
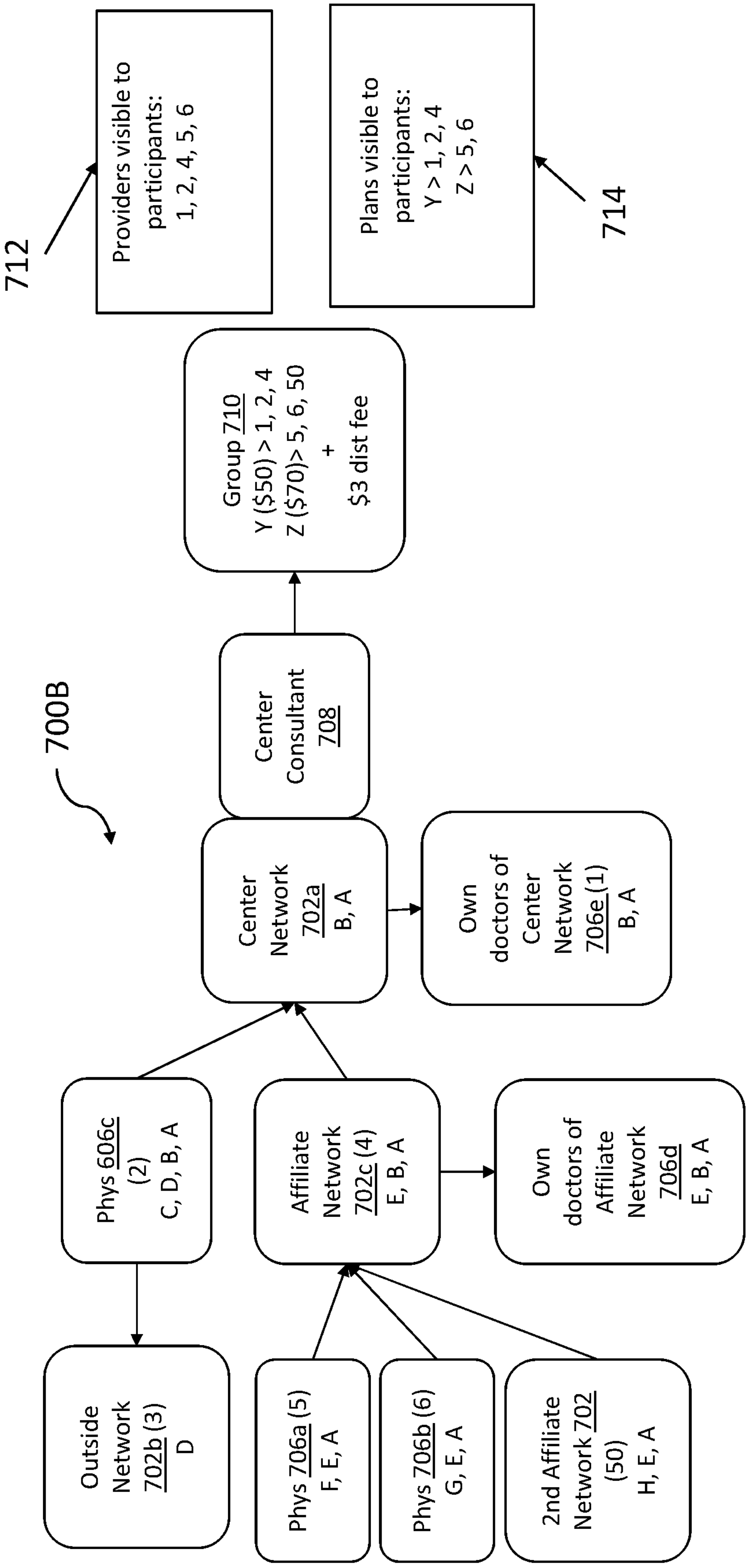
Figure 7C:
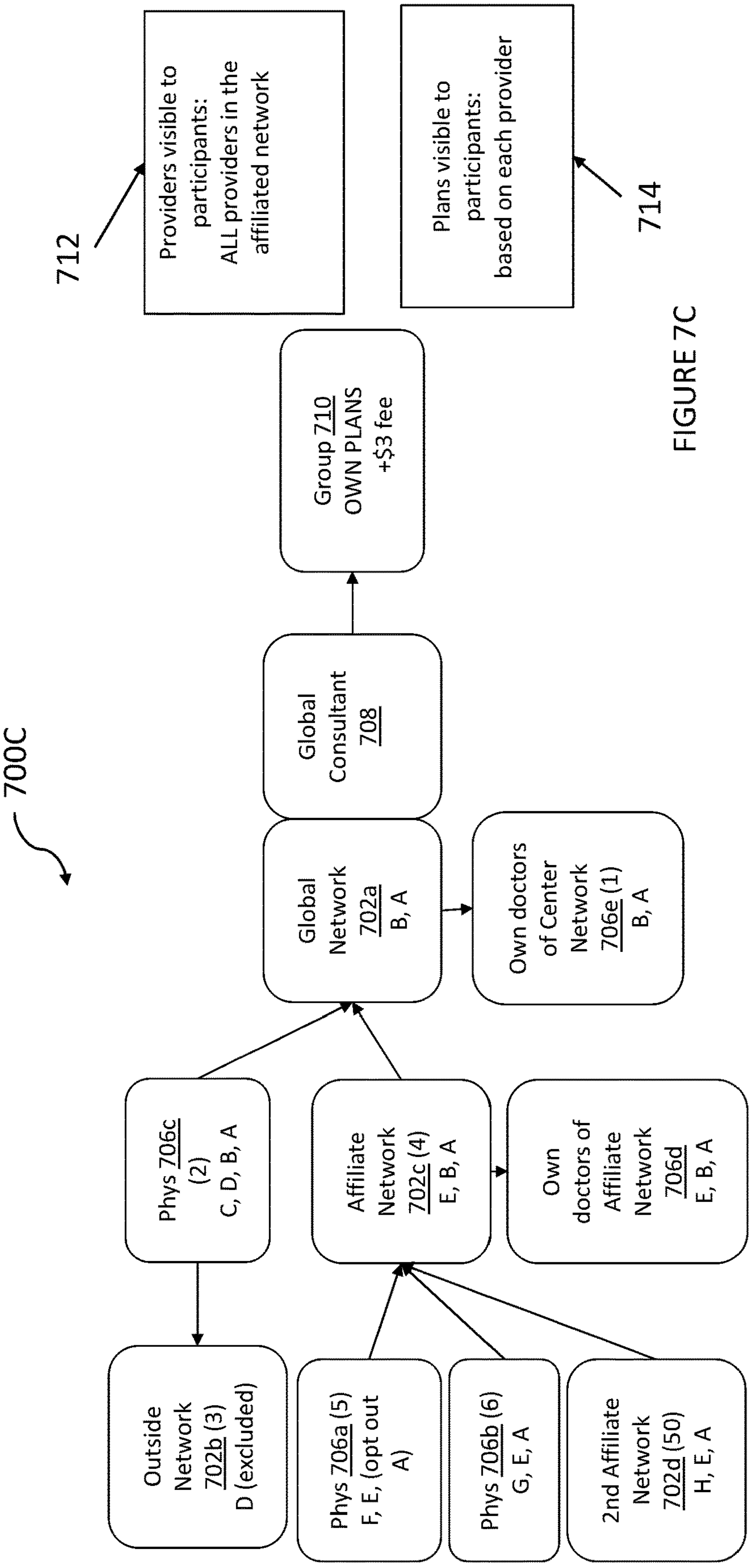

FIGS. 7A-7C depict example affiliations 700A-700C that may be created based on a network and consultant instance, such as an instance set forth in FIG. 6A or 6B. As shown in FIG. 7A, a center network 702*a* may be coupled to a center consultant device 708. In this example, providers may be identified by numbers (1, 2, 3, 4, 5, 6) and plans may be identified by letters (A, B, C, D, E, F, G, H, X). In each instance, each individual node, or service provider, may have their own plan, share their plan with another, or inherit plans from one another. In an example custom group instance, an administrator may specify which service providers 712 may be visible to users, or participants. Additionally, the example instance may be customized to include only certain plans 714. Costs or fees, that may be customized, may cause certain providers to become invisible to users associated within a custom group instance. Based on logic within the system, boundaries are created between different custom group instances, plan details, and information, or data packets including fee allocation data, is transmitted properly.

In some embodiments, a center network 702A may be coupled to independent doctors 706*e*, physician device 706*c*, and affiliate network 702*c*. A physician device 706*c* may be communicatively coupled to a further network, such as outside network 702*b*. Affiliate network 702*c* may be communicatively coupled to another affiliate network, such as affiliate network 702*d*, physician devices 706*a* and 706*b*, and the affiliates own network of physicians 706*d*. A center consultant 708 may be connected to a group device 710 that manages a group of users based on plan participation, availability, customization options, eligibility management, payment management, or the like. In an exemplary configuration, a subset of service providers among a set of service providers may be affiliated with one another and made available based on their ability to provide services in accordance with a threshold. For example, the threshold may be a certain fee rate for providing the service. The subset of service providers may then be affiliated with a certain plan and provided as a custom group instance by an administrator.

As shown in FIG. 7B, example affiliation instance 700B provides an implementation of payment management that would cause only certain plans viewable to certain participants and/or groups of participants. For example, certain plans may have multiple parameters associated therewith, such as plan pricing, provider fees, plan allowances, and other fees, for example. In some embodiments, different groups may represent different employers and therefore provide different plan levels. Based on a plan level, different providers, or clinics that encompass multiple providers, may become available, or viewable, by a participant of a group via center consultant 708. As shown and described, customized plans create network associations that rely on secure data transmission. Based on a customized plan between a group, such as group 710, and a physician device, such as device 706*b*, center network 702*e* may maintain plan details and dynamically route data packets between appropriate networked devices based on the plan.

Example instance 700C of FIG. 7C provides another example in accordance with an embodiment that provides plans that are visible to participants are based on each provider. Additionally, or alternatively, the providers visible to users, or participants, include all the providers in an affiliated network, such as affiliated network 702*c* and 702*d*.

Figure 8:
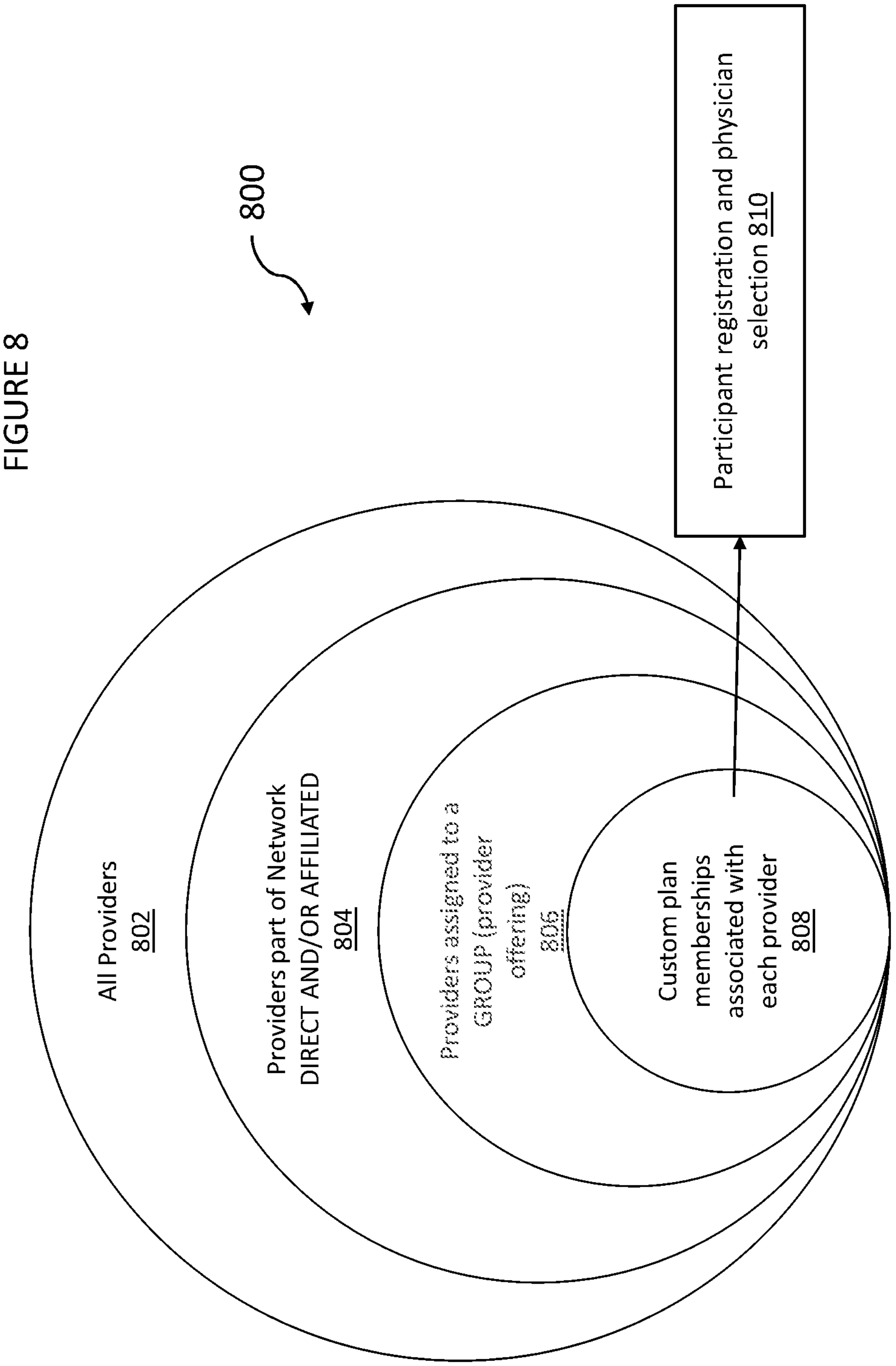
FIG. 8 illustrates an exemplary logic layer for customizable implementations in accordance with one embodiment of the present disclosure.

FIG. 8 depicts an exemplary illustration of layered provider offerings customization view 800. In some embodiments, a first layer, providers 802, may include all providers within a network, such as network 602 of FIG. 6A. The providers of 802 may include all provider, or physician, devices communicatively connected to network 602, such as via direct network connection or via other devices, such an affiliate network device, or the like. The next layer, layer 804, may include providers, or physician devices, associated with a certain network, such as network 602 of FIG. 6A, for example. The next layer, layer 806, may include providers, or physician devices, associated with a certain group, such as group 610*c* of FIG. 6A, for example. The next layer, layer 808, may include all custom plan memberships associated with each provider, such as group 610*b* of FIG. 6A, for example. A custom plan membership may be created by a user or participant based on the user's registration and physician selection in step 810, for example.

Figure 9:
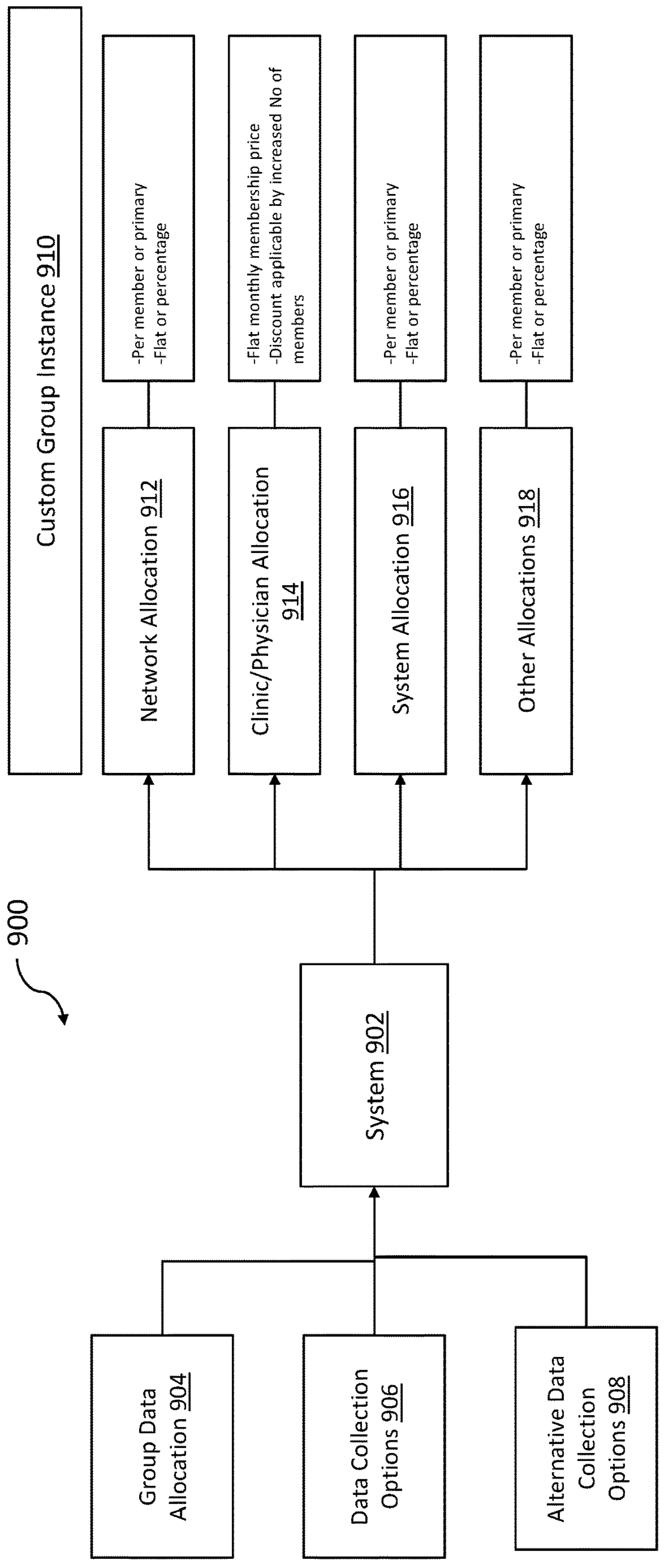
FIG. 9 illustrates an exemplary data routing workflow for at least one instance of a network affiliation in accordance with embodiments of the present disclosure.

FIG. 9 depicts an exemplary process 900 of data packet division and distribution by a system, such as system 902, for an exemplary group instance 910. System 902 may be a service device, such as MLAR device 210 of FIG. 2. An exemplary group instance 910 may include a system 902 that may be configured to receive data packets from multiple data sources: 1) group allocation data 904, 2) data collection options 906, and 3) from alternative data collection sources 908. In accordance with group instance 910, data packets received by system 902 may be divided and allocated among multiple destinations. The multiple destinations may include, but are not limited to, network allocation 912, clinic/physician allocation 914, system allocation 916, and other allocations 918. Allocations may be based on a myriad of factors including, but not limited to, per member, per primary, a monthly membership allocation, or the like.

Figure 10:
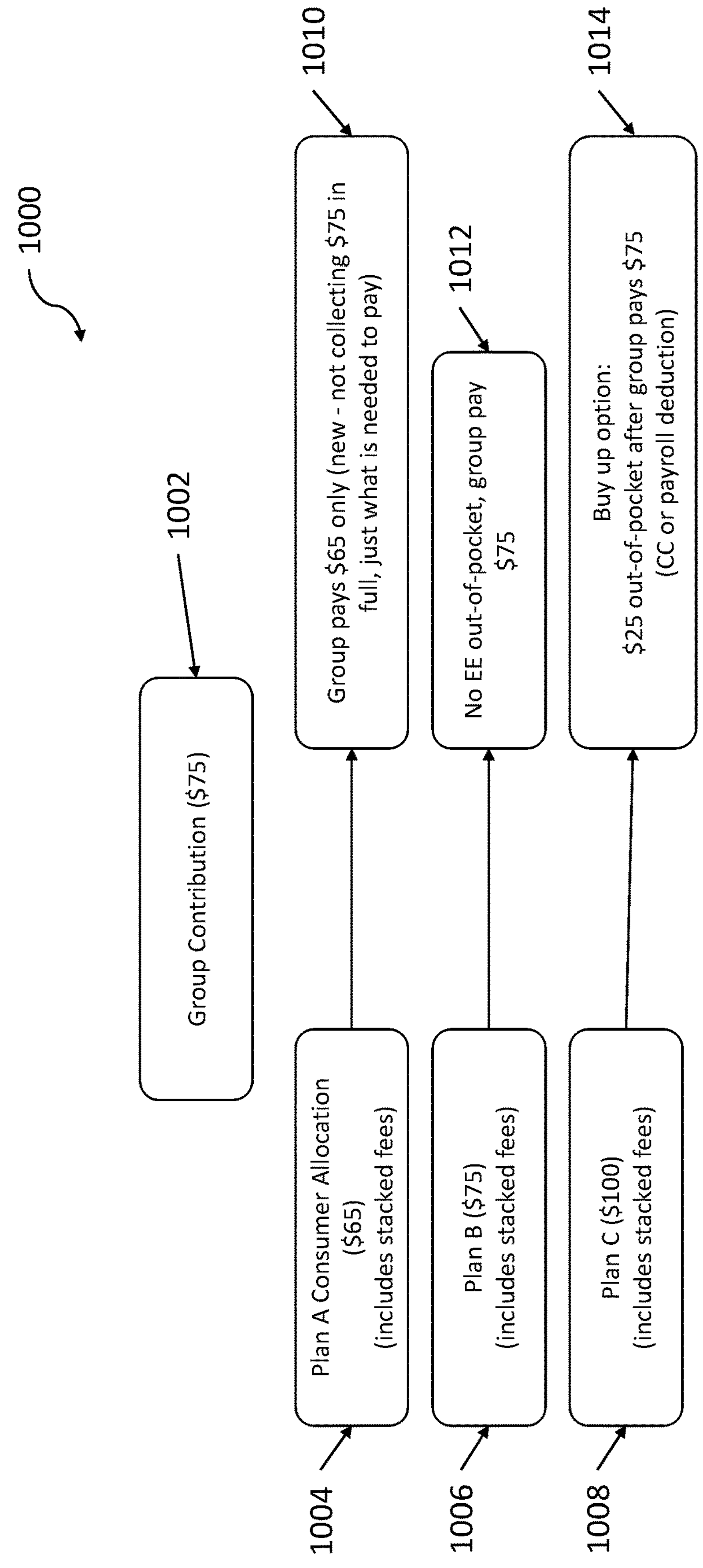
FIG. 10 illustrates exemplary routing of data packets within a group instance in accordance with one embodiment of the present disclosure.

FIG. 10 depicts an example workflow 1000 of an allocation of data among networked devices, such as those within a group instance described herein. In this example, data may include out-of-pocket calculations and capitated payments. For example, out-of-pocket fees may be collected from participants. Fees may be collected via credit card, debit card, payroll deduction, or the like. Prices may be determined based on plan details. For example, final consumer prices may include stacked fees for third party allocations. Additionally, or alternatively, group contributions, plan diversity and price, and third-party allocations may be customized per group and/or inherited to a participant's offer. In the example shown in FIG. 10, a group contribution 1002 may be of a certain value, such as $75. Multiple plans may be included, such as Plan A 1004, Plan B 1006, and Plan C 1008. Based on customization, plan fees that exceed the group contribution 1002, such as Plan C 1008, may trigger a buy up option 1014. In another example, if a plan fee does not exceed contribution, such as Plan A 1004, only the plan fee 1010 would be collected via the group contribution 1002. In yet another example, if a plan fee equals contribution, such as Plan B 1006, no out-of-pocket contribution 1012 would be required of a participant of the plan.

Figure 11:
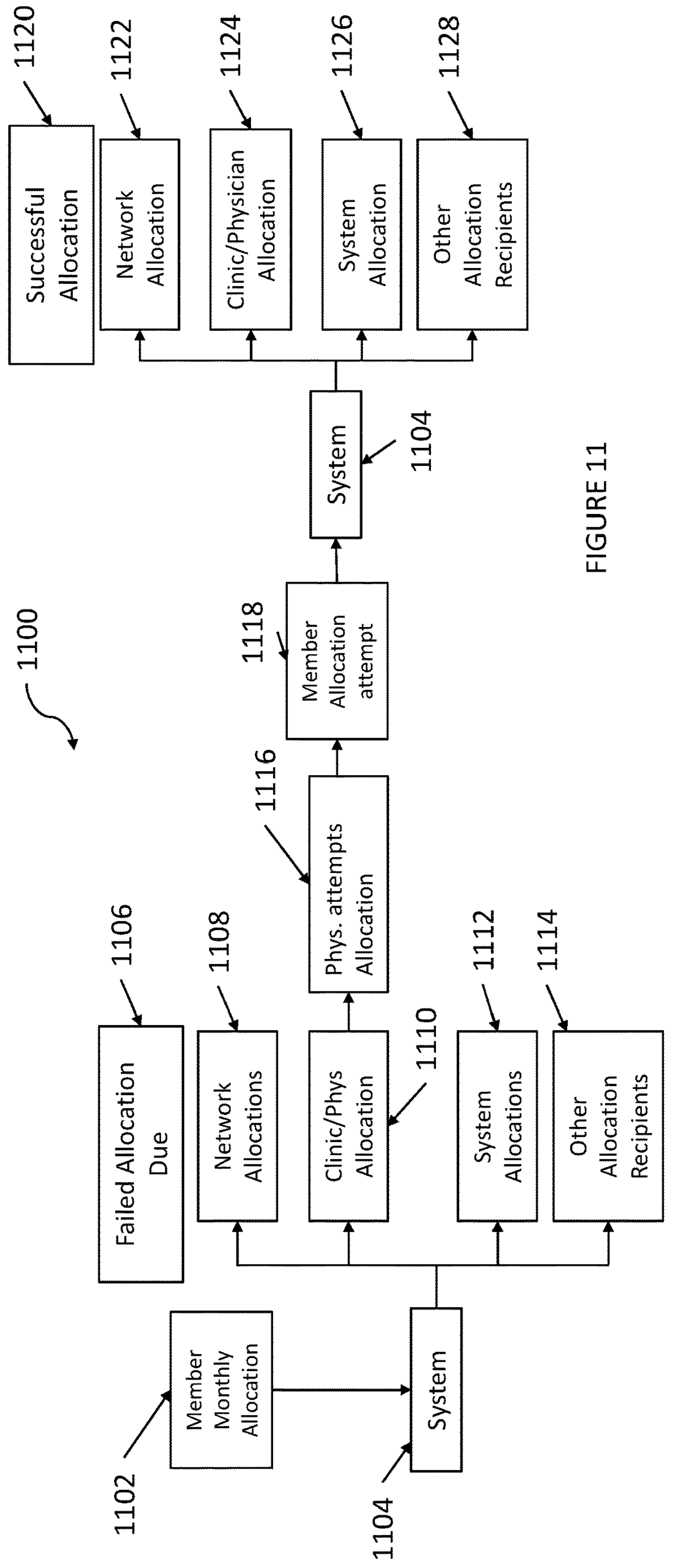
FIG. 11 illustrates exemplary routing of data packets for the reconciliation of debt in accordance with one embodiment of the present disclosure.

FIG. 11 illustrates an example allocation of data process 1100 in the event a group contribution does not cover all allocations required by a group instance. In this example, a participant may provide data for allocation, such as via a monthly allocation contribution 1102, to system device 1104. In some examples, a failed attempt 1106 to perform an allocation may occur. A failed allocation to one or more of network allocations 1108, clinic/physician allocation 1110, system allocation 1112, and/or other allocation recipients 1114. An alternative allocation, such as one by a physician attempt 1116 and member allocation attempt 1118, may be performed. In this example, system 1104 may experience a successful allocation 1120. In this example, a successful allocation 1120 may include the dividing of packet data among network allocation 1122, clinic/physician allocation 1124, system allocation 1126, and other allocation recipients 1128, for example.

Figure 12A:
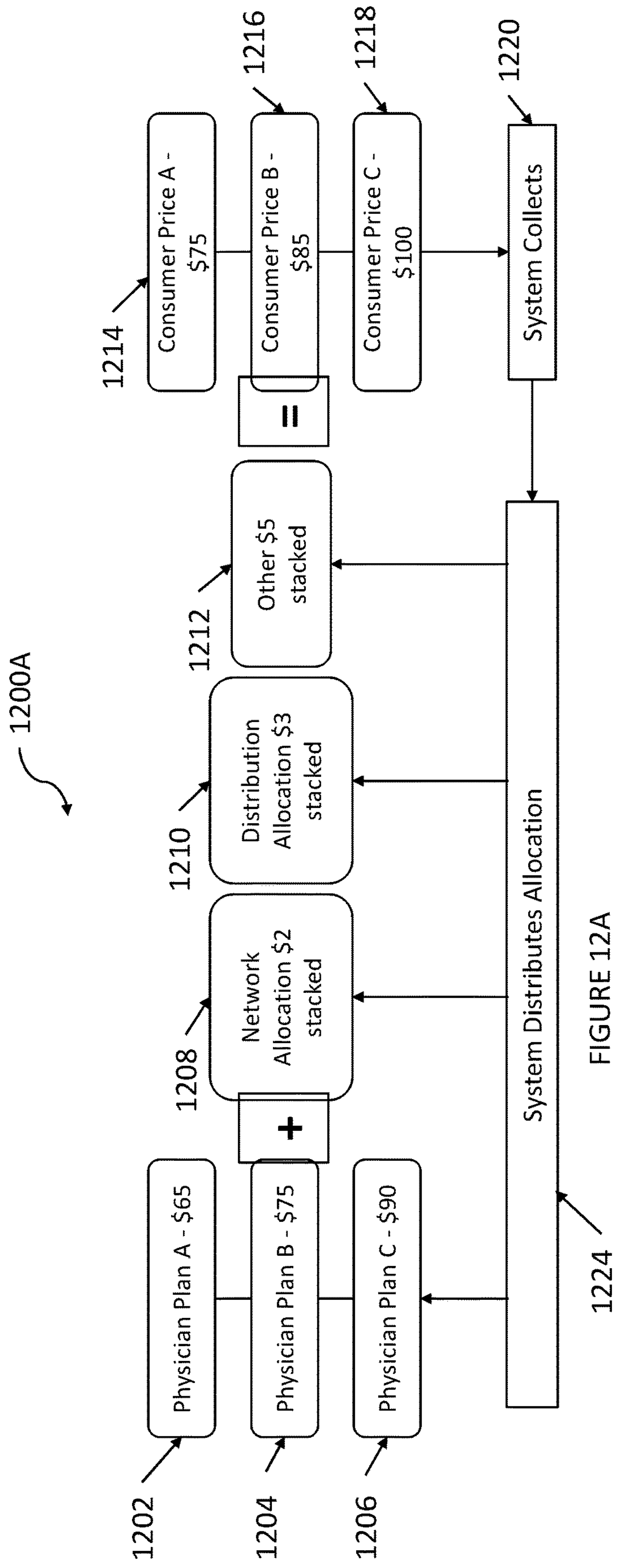
FIGS. 12A and 12B illustrate the exemplary routing of data packets for providing stacked or non-stacked fees in accordance with embodiments of the present disclosure.

FIG. 12A provides an example of an allocation distribution 1200A in an instance where stacked allocation may be use where groups and members of a plan may be provided with a consumer allocation that may include one or more additional allocation requirements. Once allocations are collected 1220, the system 1224 may distribution appropriate allocations. Plans may include different allocation requirements 1202, 1204, and 1206. In addition to plan requirements, additional allocation amounts may be determined, as shown in elements 1208, 1210, and 1212. System 1224 may collect allocation contributions based on different prices shown in 1214, 1216, and 1218.

Figure 12B:
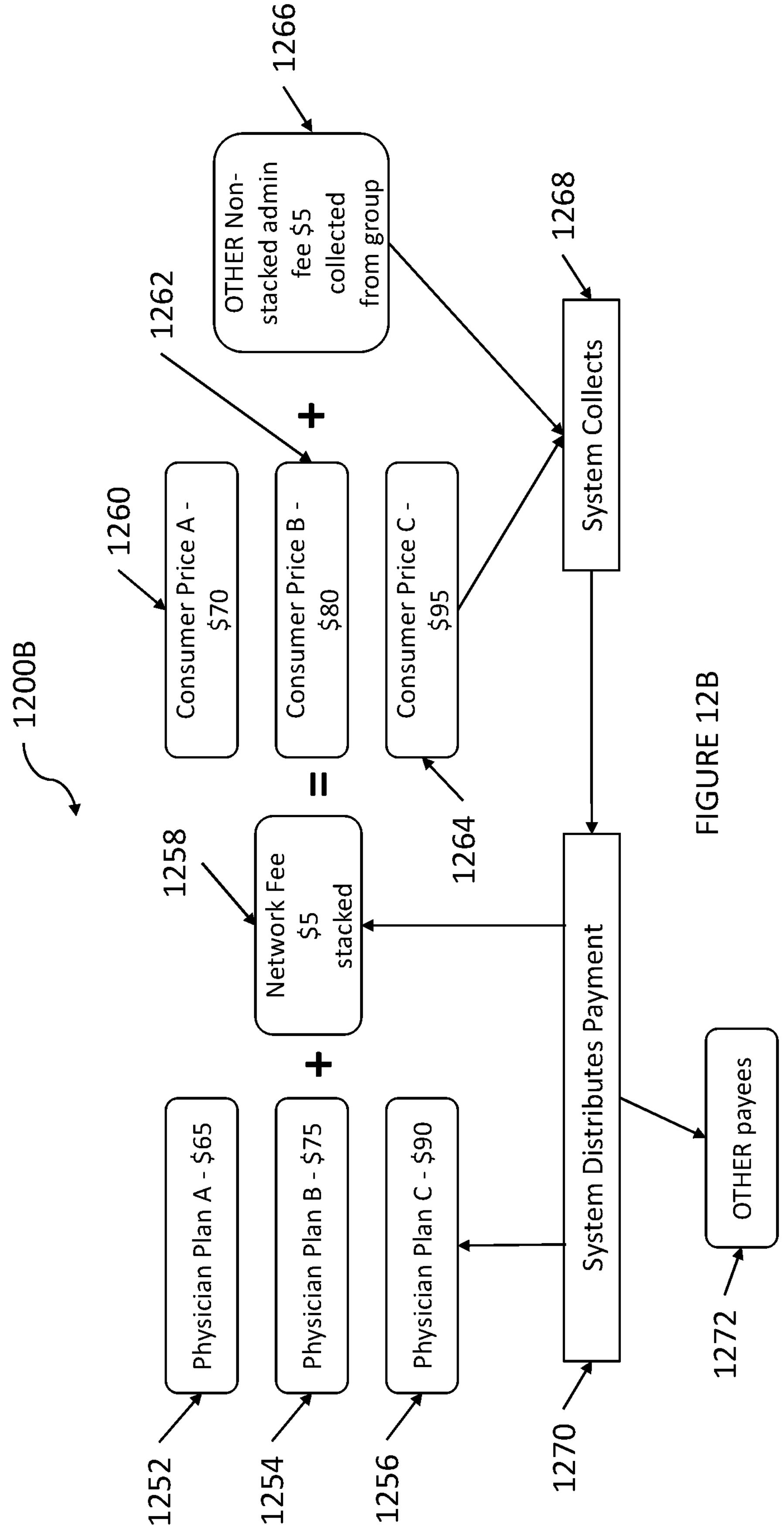

FIG. 12B provides another example of allocation distribution, distribution 1200B in another exemplary instance. In 1200B, system may collect allocations 1268 from groups, such as groups 1260, 1262, and 1264. Further, the system may collect other allocations from a group, such as other allocations 1266. Once collected, a system may distribute allocations 1270 to the system, other payees 1272, and to appropriate physician devices in accordance with a plan, such as physician devices 1252, 1254, and 1256. In this example, one or more allocations may be non-stacked.

Figure 13:
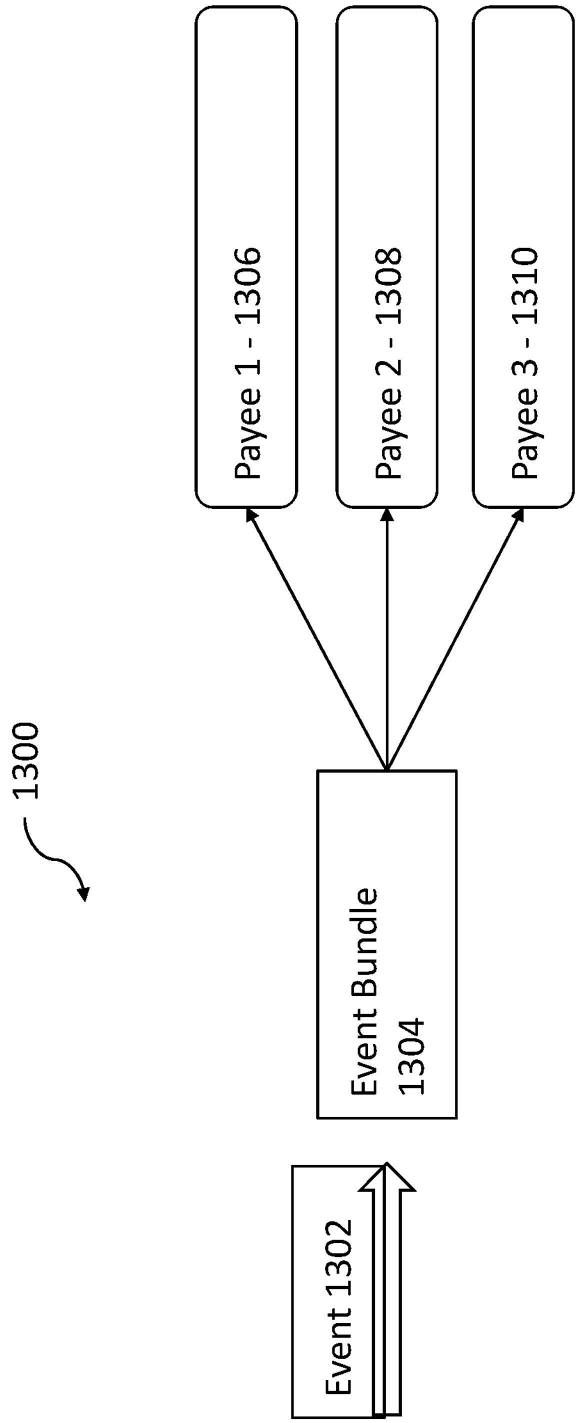
FIG. 13 illustrates an exemplary event for the routing of data packets in accordance with at least one embodiment of the present disclosure.

FIG. 13 illustrates an example event bundler process 1300. In some embodiments, an event bundler may implement the dissemination of information in a network based on the occurrence of an event. An event bundler may control the distribution or propagation of information via data packets within a network based on a customized plan described herein. For example, an event may occur in step 1302. In step 1304, data packets pertaining to the event may be bundled. In step 1306, the data packets may be divided and distributed among a plurality of endpoints within a network, such as payees 1306, 1308, and 1310. In some embodiments, data pertaining to a plan, such as plan membership modifications, changes being implemented to a plan, or the like, may be transmitted to devices of a network. In some embodiments, an event bundle may include fee disbursements to be made to payees 1306, 1308, and 1310. Additionally, prior to disbursement over a network, a plan provider may confirm and/or approve portions of the event bundle with respect to total amounts to be paid to each of the payees, for example. In some embodiments, discounts may be applied to payments intended for payees. Discounts may be identified via different types of codes, such as CPT codes, or the like.

In some embodiments, an event 1302 may occur on a regular basis. For example, an event may be scheduled to occur on a weekly, monthly, or even yearly basis. Additionally, or alternatively, a server system, such as server 210 (shown in FIG. 2), may be configured to manage the dissemination of data, in the form of data packets, on a scheduled basis (e.g., monthly) to all users on a network considered to be relevant. Relevant network users may include members of a custom group instance. Further, relevant network users may be sub-groups of members within a custom group instance (e.g., nuclear family members and their providers).

Figure 14A:
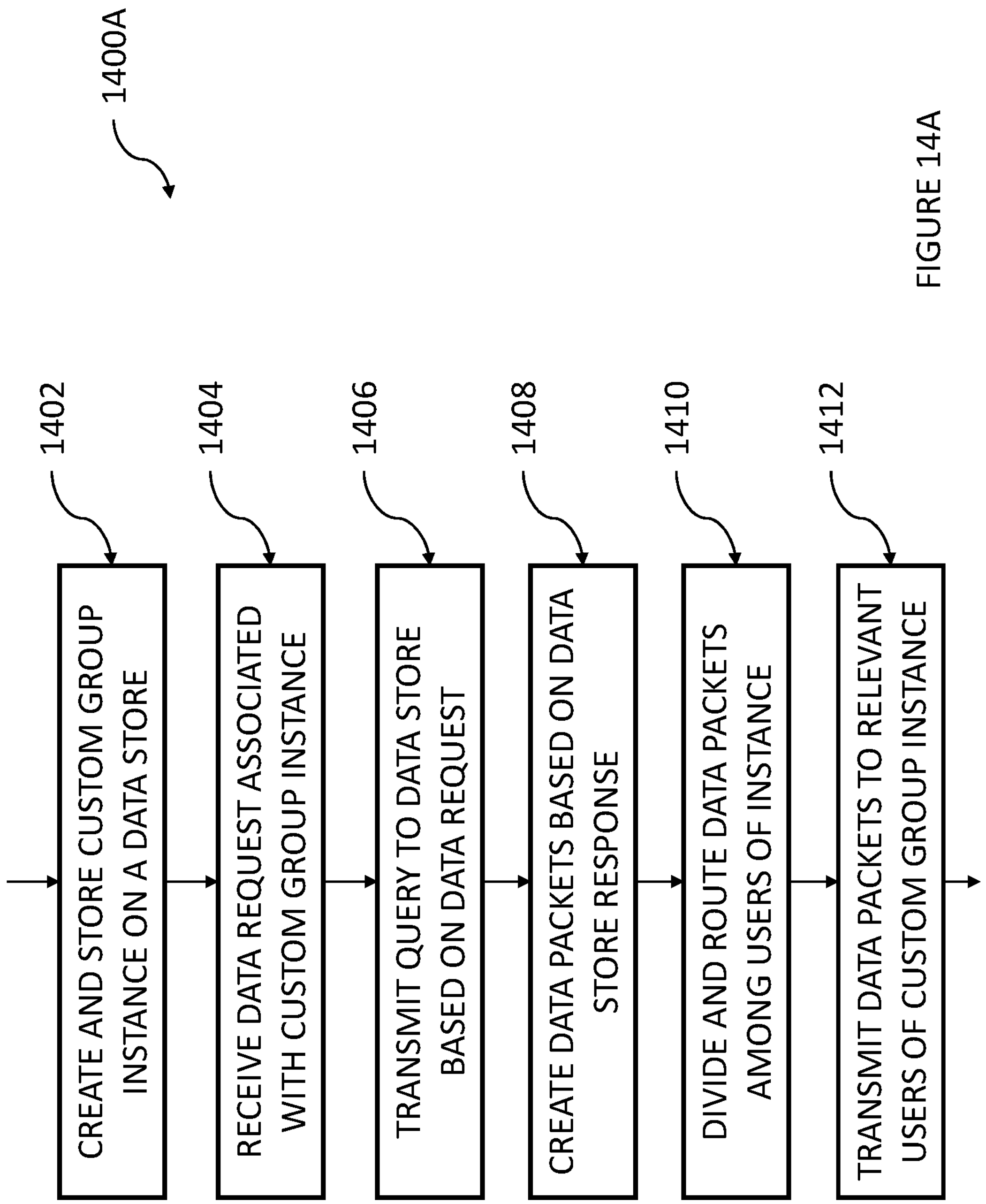
FIGS. 14A and 14B illustrate exemplary processes for the multi-layer adaptive routing of data packets by the MLAR computing device illustrated in FIG. 2.

FIG. 14A illustrates a process 1400A for the routing of data packets in accordance with one embodiment of the disclosure. In the exemplary embodiment, process 1400A may be performed by MLAR server 210 (shown in FIG. 2). In other embodiments, process 1400A may be performed by a plurality of computer devices.

In the exemplary embodiment, MLAR server 210 creates and stores 1402 a custom group instance on a data storage device. The data storage device may be database 220 (shown in FIG. 2), for example. The custom group instance may include a plurality of users associated with computing devices, such as devices 205 (shown in FIG. 2), a plurality of physicians or healthcare providers associated with computing devices, such as healthcare provider computer devices 225 (shown in FIG. 2), for example. Data may be stored pertaining to members of the custom group instance. For example, stored data may include, but is not limited to, healthcare plan data, provider fees, payment information including available methods of payment, member plan data including primary plan holder information and dependents, if applicable, fee collection frequency data, and fee disbursement frequency data. In some embodiments, the custom group instance may evolve over time based on provider participation, user enrollment status, or the like.

In the exemplary embodiment, MLAR server 210 receives 1404 data requests from connected devices, such as device 205 (shown in FIG. 2). Data requests may include, but are not limited to, membership enrollment, user account modification requests (e.g., change or provider selection, customized provider selection for different family members under same plan, addition/removal of family members, coverage changes, plan selection based on eligibility, payment disbursement change requests, and termination of plan membership requests, for example. In some embodiments, eligibility management may be performed via a data extraction process. For example, a new member of the instance may submit an electronic form that includes one or more data fields to provide personal information (e.g., name, address, SSN, employment status, etc.). The electronic form may be of a certain file format, such as a PDF or an 834 file. Additionally, MLAR server 210 may be configured to, via a data extraction process, initiate one or changes or alterations to the custom group instance based on information provided by the electronic form. In step 1406, MLAR server 210 may transmit the query to the custom group instance to enact any changes or modifications provided by the data request.

In the exemplary embodiment, MLAR server 210 may receive a response from the data store, such as data that was requested of the custom group instance or an acknowledgement that a modification was performed per the data request. MLAR server 210 may then create 1408 a plurality of data packets based on the information received from the data store. MLAR server 210 may then divide and route 1410 the plurality of data packets among relevant users of the custom group instance. Finally, MLAR server 210 may transmit 1412 the plurality of divided data packets to the relevant users of a custom group instance.

Figure 14B:
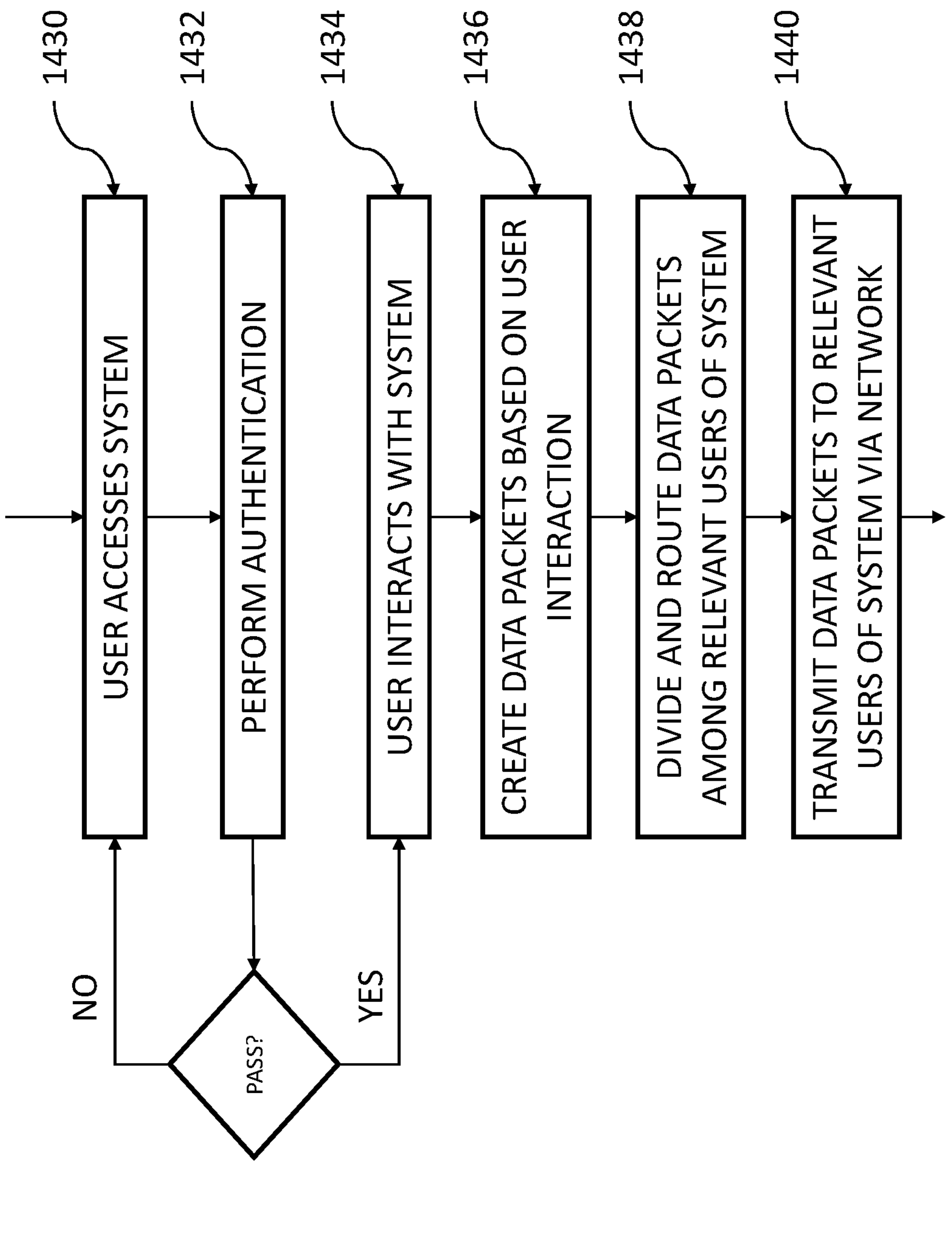

FIG. 14B illustrates another process 1400B for the routing of data packets in accordance with one embodiment of the disclosure. In the exemplary embodiment, process 1400B may be performed by MLAR server 210 (shown in FIG. 2). In other embodiments, process 1400B may be performed by a plurality of computer devices.

In the exemplary embodiment, MLAR server 210 may receive a request from a user, such as a user of computing device 205, to access 1430 the system. The user may need to perform data modifications to a custom group instance the user is associated with, for example. Prior to being given access, the MLAR server 210 performs 1432 authentication of the user. This may require the user to provide a username and password, complete multi-factor authentication, or provide other types of user identifying credentials. Once authenticated, MLAR server 210 allows the user to interact with the system in step 1434. The user's interaction may be performed via a dashboard interface or graphical user interface (GUI) displayed on the user's device, such as a display of device 205. The user interaction may include, but is not limited to, custom plan enrollment, member plan updates (e.g., life event, addition/removal of dependent, etc.), payment plan enrollment, or the like. Based on the interaction event, MLAR server 210 may create 1436 a plurality of data packets to be disseminated among a plurality of users considered to be relevant. For example, relevant users may include those closely associated with the user that performed the interaction that are within the same custom group instance, are related to the user, are an employer of the user, or are service providers of the user. In some embodiments, the interaction may cause an event to be created that causes the allocation of funds among a plurality of service providers that have provided services to the user in accordance with a custom group plan that the user sub scribes to.

In the exemplary embodiment, MLAR server 210 may divide and route 1438 the plurality of data packets among relevant users of the custom group instance. Finally, MLAR server 210 may transmit 1440 the plurality of divided data packets to the relevant users of a custom group instance.

Technical Solutions

At least one of the technical solutions to the technical problems provided by this system may include: (i) reducing data network traffic between network devices belonging to custom group instances; (ii) using rules to route data packets to appropriate network devices, such as devices belonging to custom group instances; (iii) bundling data network packets addressed to common networked devices; and (iv) providing instant notifications and updates to relevant networked devices associated with notifications and updates, such as updates made to a custom group instance.

At least one of the technical solutions to the technical problems provided by this system may include: (i) reducing the number of payments that need to be made to healthcare providers; (ii) reducing the message traffic communicating between the employer or healthcare plan administrator and each individual healthcare provider; (iii) using rules to properly route payments to the appropriate healthcare provider; and (iv) reducing the amount of risk associated with a healthcare plan; (v) stabilizing payments for a healthcare plan; and (vi) stabilizing income for a healthcare provider.

Implementation Examples

The methods and systems described herein may be implemented using computer programming or engineering techniques including computer software, firmware, hardware, or any combination or subset thereof, wherein the technical effects may be achieved by performing at least one of the following steps: (a) store, on a database, a custom group instance including a network of a plurality of service providers and a consultant including a plurality of user groups; (b) receive a data request from at least one of a plurality of users of one of the plurality of user groups of the custom group instance; (c) submit a query to the database based at least in part on the data request; (d) create, based on a response from the database based on the query, data packets and divide and route the data packets among at least some of plurality of users within the custom group instance; and (e) transmit the divided data packets to the at least some of the plurality of users; (f) wherein the data request is sent to the MLAR computing device in response to an event; (g)

wherein the event occurs in response to a data extraction process initiated by one of the at least one of the plurality of users; (h) wherein the data extraction process includes extracting data from an Electronic Data Interchange (EDI) 834 file; (i) wherein the event occurs in response to a modification made to the custom group instance; and (j) wherein the data packets are divided and routed based on a customized plan of the custom group instance; and (k) wherein the database stores and maintains: a plurality of user records associated with the plurality of users; a plurality of provider records associated with a plurality of providers; and one or more affiliations between at least some of the plurality of users and some of the plurality of providers based on a customized plan of the custom group instance.

ADDITIONAL CONSIDERATIONS

The computer-implemented methods discussed herein may include additional, less, or alternate actions, including those discussed elsewhere herein. The methods may be implemented via one or more local or remote processors, transceivers, servers, and/or sensors, and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an exemplary embodiment, the system is executed on a single computer system, without requiring a connection to a sever computer. In a further embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom), or any other type of operating system environment. The application is flexible and designed to run in various different environments without compromising any major functionality.

In some embodiments, the system includes multiple components distributed among a plurality of computer devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes. The present embodiments may enhance the functionality and functioning of computers and/or computer systems.

As used herein, an element or step recited in the singular and preceded by the word "a" or "an" should be understood as not excluding plural elements or steps, unless such exclusion is explicitly recited. Furthermore, references to "example embodiment," "exemplary embodiment," or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A multi-layer adaptive routing (MLAR) computing device for the routing of packet data comprising at least one processor in communication with a memory device, wherein the at least one processor is configured to:

store, on a database, a custom group instance including a network of a plurality of healthcare service providers and a consultant including a plurality of user groups configured to use services provided by the plurality of healthcare service providers, wherein each user group of the plurality of user groups are defined by a plurality of group parameters, wherein each user group of the plurality of user groups includes a plurality of patients that may access the plurality of healthcare service providers based upon the corresponding plurality of group parameters;

receive a new patient data request from at least one of a plurality of users of one of the plurality of user groups of the custom group instance, the new patient data request including information to add a new patient to one or more user groups of the custom group instance;

submit a query to the database based at least in part on the new patient data request, wherein the query is configured to add the new patient to the one or more user groups of the custom group instance;

receive, from the database, a response to the query submitted to the database including an acknowledgement of the new patient in the database;

determine at least some of the plurality of users and the plurality of healthcare service providers within the custom group instance to route information in the response to;

create, based on the response from the database, data packets and routing information for the data packets among at least some of plurality of users and the plurality of healthcare service providers within the custom group instance based upon the determination; and transmit the data packets to the at least some of the plurality of users and the plurality of healthcare service providers based upon the routing information.

2. The MLAR computing device of claim 1, wherein the new patient data request is sent to the MLAR computing device in response to an event.

3. The MLAR computing device of claim 2, wherein the event occurs in response to a data extraction process initiated by one of the at least one of the plurality of users.

4. The MLAR computing device of claim 3, wherein the data extraction process includes extracting data from an Electronic Data Interchange (EDI) 834 file.

5. The MLAR computing device of claim 2, wherein the event occurs in response to a modification made to the custom group instance.

6. The MLAR computing device of claim 1, wherein the data packets are divided and routed based on a customized plan of the custom group instance.

7. The MLAR computing device of claim 1, wherein the database stores and maintains:

a plurality of user records associated with the plurality of users;

a plurality of provider records associated with a plurality of providers; and one or more affiliations between at least some of the plurality of users and some of the plurality of providers based on a customized plan of the custom group instance.

8. A computer-implemented method for the dynamic routing of packet data, the computer-implemented method implemented by a multi-layer adaptive routing (MLAR) computing device including at least one processor in communication with a memory device, the method comprising:

storing, on a database, a custom group instance including a network of a plurality of healthcare service providers and a consultant including a plurality of user groups configured to use services provided by the plurality of healthcare service providers, wherein each user group of the plurality of user groups are defined by a plurality of group parameters, wherein each user group of the plurality of user groups includes a plurality of patients that may access the plurality of healthcare service providers based upon the corresponding plurality of group parameters;

receiving a payment data request from at least one of a plurality of users of one of the plurality of user groups of the custom group instance, the payment data request including a request to provide payment to one or more healthcare service providers of the plurality of healthcare service providers based on the customer group instance;

submitting a query to the database based at least in part on the payment data request, wherein the query is configured to determine payment information for the one or more healthcare service providers of the plurality of healthcare service providers;

receiving, from the database, a response to the query submitted to the database including the payment information for the one or more healthcare service providers;

determining the plurality of healthcare service providers to route payments to;

creating, based on the response from the database, data packets including payments and routing information for the data packets the plurality of healthcare service providers within the custom group instance based upon the determination; and transmitting the data packets to the plurality of healthcare service providers based upon the routing information.

9. The computer-implemented method of claim 8, wherein the payment data request is sent to the MLAR computing device in response to an event.

10. The computer-implemented method of claim 9, wherein the event occurs in response to a data extraction process initiated by one of the at least one of the plurality of users.

11. The computer-implemented method of claim 10, wherein the data extraction process includes extracting data from an Electronic Data Interchange (EDI) 834 file.

12. The computer-implemented method of claim 9, wherein the event occurs in response to a modification made to the custom group instance.

13. The computer-implemented method of claim 8, wherein the data packets are divided and routed based on a customized plan of the custom group instance.

14. The computer-implemented method of claim 8, wherein the database stores and maintains:

a plurality of user records associated with the plurality of users;

a plurality of provider records associated with a plurality of providers; and one or more affiliations between at least some of the plurality of users and some of the plurality of providers based on a customized plan of the custom group instance.

15. At least one non-transitory computer readable medium having instructions embodied thereon, wherein when executed by a multi-layer adaptive routing (MLAR) computing device including at least one processor in communication with a memory device, the computer-executable instructions cause the at least one processor to:

store, on a database, a custom group instance including a network of a plurality of service providers and a consultant including a plurality of user groups configured to use services provided by the plurality of service providers, wherein each user group of the plurality of user groups are defined by a plurality of group parameters, wherein the plurality of user groups may access the plurality of service providers based upon the corresponding plurality of group parameters;

receive a data request from at least one of a plurality of users of one of the plurality of user groups of the custom group instance, the data request including one or more modifications to at least one parameter of the plurality of group parameters for the custom group instance;

submit a query to the database based at least in part on the data request, wherein the query is configured to enact the one or more modifications to the at least one parameter;

receive, from the database, a response to the query submitted to the database including an acknowledgement of the one or more modifications in the database;

determine at least some of the plurality of users within the custom group instance to route information in the response to;

create, based on the response from the database, data packets and routing information for the data packets among at least some of plurality of users within the custom group instance based upon the determination; and transmit the data packets to the at least some of the plurality of users based upon the routing information.

16. The at least one non-transitory computer readable medium of claim 15, wherein the data request is sent to the MLAR computing device in response to an event.

17. The at least one non-transitory computer readable medium of claim 16, wherein the event occurs in response to a data extraction process initiated by one of the at least one of the plurality of users.

18. The at least one non-transitory computer readable medium of claim 16, wherein the event occurs in response to a modification made to the custom group instance.

19. The at least one non-transitory computer readable medium of claim 15, wherein the data packets are divided and routed based on a customized plan of the custom group instance.

20. The at least one non-transitory computer readable medium of claim 15, wherein the database is configured store and maintain:

a plurality of user records associated with the plurality of users;

a plurality of provider records associated with a plurality of providers; and one or more affiliations between at least some of the plurality of users and some of the plurality of providers based on a customized plan of the custom group instance.

* * * * *